(12) United States Patent
Kratz

(10) Patent No.: US 6,310,039 B1
(45) Date of Patent: Oct. 30, 2001

(54) ANTINEOPLASTIC CONJUGATES OF TRANSFERRIN, ALBUMIN AND POLYETHYLENE GLYCOL

(76) Inventor: Felix Kratz, Mühlenweg 3, D-79232 March (DE)

(*) Notice: Subject to any disclaimer, the term of this patent is extended or adjusted under 35 U.S.C. 154(b) by 0 days.

(21) Appl. No.: 09/254,598

(22) PCT Filed: Sep. 9, 1997

(86) PCT No.: PCT/DE97/02000

§ 371 Date: May 21, 1999

§ 102(e) Date: May 21, 1999

(87) PCT Pub. No.: WO98/10794

PCT Pub. Date: Mar. 19, 1998

(30) Foreign Application Priority Data

Sep. 11, 1996 (DE) ............................................. 196 36 889

(51) Int. Cl.[7] ........................... A61K 38/38; A61K 47/48
(52) U.S. Cl. ............................ 514/8; 424/649; 514/21; 514/34; 514/45; 514/49; 514/249; 514/283; 514/564; 530/408
(58) Field of Search .............................. 424/649; 514/2, 514/8, 12, 21, 34, 45, 46, 47, 48, 49, 51, 249, 283, 492, 564; 530/362, 363, 404, 408; 536/4.1, 6.4, 7.1, 16.8, 17.2, 18.1, 27.21, 28.4; 562/449; 544/261; 546/51; 423/413

(56) References Cited

U.S. PATENT DOCUMENTS

| | | | |
|---|---|---|---|
| 4,507,234 | * | 3/1985 | Kato et al. ................................. 514/2 |
| 4,980,457 | * | 12/1990 | Jansen et al. ........................ 530/391 |
| 5,030,620 | * | 7/1991 | Hannart et al. ......................... 514/18 |
| 5,208,021 | * | 5/1993 | Johnson et al. .................... 424/85.91 |
| 5,622,929 | * | 4/1997 | Willner et al. ............................ 514/8 |
| 5,705,363 | * | 1/1998 | Imakawa ........................... 435/69.51 |

FOREIGN PATENT DOCUMENTS

| | | |
|---|---|---|
| 41 22 210 A1 | 1/1993 | (DE) . |
| 0 359 347 A2 | 3/1990 | (EP) . |
| 0 393 575 B1 | 10/1990 | (EP) . |
| 0 495 265 A1 | 7/1992 | (EP) . |
| 0 665 020 A3 | 8/1995 | (EP) . |
| 0 745 390 A2 | 12/1996 | (EP) . |
| WO 88/00837 | 2/1988 | (WO) . |
| WO 91/01757 | 2/1991 | (WO) . |
| WO 91/08220 | 6/1991 | (WO) . |
| WO 92/02255 | 2/1992 | (WO) . |
| WO 96/39183 | 12/1996 | (WO) . |
| WO 97/39007 | 10/1997 | (WO) . |
| WO 98/13059 | 4/1998 | (WO) . |

OTHER PUBLICATIONS

Beyer et al. Synthesis of Transferrin And Albumin Conjugates . . . Eur. J. Pharm. Sci. vol. 4, Supple, 1996.*
Caliceti et al. Preparation And Properties Of Monomethoxy . . . Il Farmaco, vol. 48, No. 7, pp. 919–932, 1993.*
Kratz et al. Synthesis Of New Maleimide Derivatives . . . Bioorg. Med. Chem. Lett. vol. 7, No. 5, pp. 617–622, 1997.*
Motsenbocker et al. Photoactive Methylene Blue Dye . . . Photochem. Photobiol. vol. 58, No. 5, pp. 648–652, 1993.*
Aruna Nathan, Samuel Zalipsky and Joachim Kohn, "Strategies for Covalent Attachment of Doxorubicin to Poly(PEG–Lys), a New Water–Soluble Poly(ether urethane)," Journal of Bioactive and Compatible Polymers, vol. 9, Jul. 1994, pp. 239–251.
Junio Fujiwara, Naoki Matsumoto, Tsunehiro Kitagawa and Kuniyo Inouye, "The Use of N–(aminobenzoyloxy) succinimide as a two–level heterobifunctional agent for the preparation of hapten–protein conjugates," Journal of Immunological Methods, 1990, pp. 227–235.
Hitoshi Sezaki, Mitsuru Hashida, "Macromolecule–Drug Conjugates in Targeted Cancer Chemotherapy," CRC Critical Reviews in Therapeutic Drug Carrier Systems, vol. 1, Issue 1, p. 1–38 (1984).
Peter D. Senter, Hakan P. Svensson, George J. Schreiber, Jennifer L. Rodriguez, and Vivekananda M. Vrudhula, "Poly(ethylene glycol)–Doxorubicin Conjugates Containing β–Lactamase–Sensitive Linkers," Bioconjugate Chemical, vol. 6, No. 4, 1995, pp. 389–394.
Heejoo Lee, Hae Soon Shin, Myung Gull Lee, Man Ki Park and Chong Kook Kim, "Syntheses of Drug–macromolecule Conjugates: Conjugations of 5–Fluorouracil to Human Serum Albumin and Poly-L–lysine," 1989, Yakhak Hoen, vol. 33, No. 5, pp. 267–272.
Erland J.F. Demant, Peter Buhl Jensen, and Maxwell Sehested, "Characterization of the cooperative cross–linking of doxorubicin N–hydroxysuccinimide ester derivatives to water soluble proteins," Biochemica et Biophysica Acta. 1118 (1991), pp. 83–90.

* cited by examiner

Primary Examiner—Jeffrey E. Russel
(74) Attorney, Agent, or Firm—Burns, Doane, Swecker & Mathis, LLP

(57) ABSTRACT

Conjugates of transferrin, albumin and polyethylence glycol consisting of native or thiolated transferrin or albumin or of polyethylene glycol (MW between approximately 5,000 and 20,0000) with at least one HS—, HO— or $H_2N$ group and cytostatic compounds derived through maleinimide or N-hydroxysuccinimide ester compounds, such as doxorubicin, daunorubicin, epirubicin, idarubicin, mitoxandrone, chloroambucil, melphalan, 5-fluorouracyl, 5'-desoxy-5-fluorouridine, thioguanine, methotrexate, paclitaxel, docetaxel, topotecan, 9-aminocamptothecin, etoposide, teniposide, mitopodoside, vinblastine, vincristine, vindesine, vinorelbine or a compound of general formula A, B, C or D, where n=0–6, X=—$NH_2$, —OH, —COOH, —O—CO—R—COR*, —NH—CO—R—COR*, where R is an aliphatic carbon chain with 1–6 carbon atoms or a substituted or unsubstituted phenylene group and R* H, phenyl, alkyl with 1–6 carbon atoms.

9 Claims, No Drawings

ANTINEOPLASTIC CONJUGATES OF TRANSFERRIN, ALBUMIN AND POLYETHYLENE GLYCOL

FIELD OF THE INVENTION

This invention relates to tumor-inhibiting conjugates of proteins and polymers consisting of a suitable carrier system and cytostatic compounds. Further, the invention relates to methods for the production of such conjugates and the use of these. Immuno-conjugates or conjugates of protein or of polymer are compounds which consist of a suitable carrier substance, such as, for example, an antibody, a growth factor, a structure similar to hormones or peptides, a protein or a polymer, and one or more cytotoxic active substances such as, for example, cytostatics, toxins or radioactive isotopes. The carrier substances have, as a rule, the characteristic of preferably accumulating in the tumor tissue, so that in this way also the active substance bound to the carrier substance accumulates in the tumor tissue and thus a selective anti-tumor therapy is achieved. Chemoimmuno-conjugates are conjugates of carrier substances and cytostatic compounds, wherein the carrier, as a rule, is an antibody.

PRIOR ART

The cytostatics currently used against cancers have a series of strong systemic side-effects and do not exhibit accumulation in the tumor tissue, so that new derivatives and formulations are being researched which make selective anti-tumor therapy possible. For this purpose, chemoimmuno-conjugates or conjugates of proteins or of polymers consisting of one suitable carrier substance or cytostatics are being developed.

As carrier substances, among others, antibodies, growth factors, serum proteins, structures similar to hormones or peptides, or polymers are considered, for which, as a rule, an accumulation in the tumor tissue is known (Mägerstädt, M.: Antibody Conjugates and Malignant Disease, Library of Congress 1990: Chadwick, C. M.: Receptors in Tumour Biology, Cambridge University Press, 1984, Seymour, L. W. CRC Crit. Rev. Ther. Drug Carrier Sys. (1992), 9, 135–187; Maeda, H.; Matsumura, Y . . . CRC Crit. Rev. Ther. Drug Carrier Sys. (1989), 6, 193–210).

The present invention comprises human serum transferrin and serum albumin as carrier proteins, of which the accumulation in the tumor tissue is documented (Ward, S. G. Taylor, R. C.: 1–54, in Metal-Based Drugs (Gielen, M. F. (Ed.)), Freund Publishing House Ltd, 1988; Sinn, H., Schrenk, H. H., Friedrich, A., Schilling, U. and Maier-Borst, W. (1990), Nucl. Med. Biol. Vol. 17(8), 819–827) as well as polyethylene glycols (PEGs) as carriers of cytostatic compounds (Topchieva, I. N. (1990), Polym. Sci. USSR 32, 833–851; Poly(ethylene glycol) Chemistry: Biotechnical and Biomedical Applications (1992), Ed. J. M. Harris, Plenum Press, New York). PEGs are, due to their bio-compatibility, their good water-solubility and synthetic divergence, very suitable for the development of therapeutic polymer conjugates. In recent years, PEGs have been conjugated mainly with medically significant proteins and enzymes (Overview in Topchieva, I. N. (1990), Polym. Sci. USSR, 32, 833–851). The production of chemoimmuno-conjugates and conjugates of proteins or of polymers occurs generally either through direct coupling of carrier substance and active substance or with the help of spacer groups, so-called homo- or heterobifunctionial reagents. Until now, mainly the method of direct coupling has been used which, however, often leads to polymeric products and not-unequivocally-defined conjugates. Recently, several chemoimmuno-conjugates (European Patent Application EP 91-117535 911615, European Patent Application EP 90-109268 900516, PCTF International Patent Application WO 90-CA251 900809, British (UK) Patent Application GB 83-5104 830224 and European Patent Application EP 89-102370 890210), which were produced using specific bifunctional reagents, were suggested as cytostatically effective media. Furthermore, from DE 41 22 210 A1, conjugates of tumor-active compounds with transferrin or albumin are known, wherein the tumor-active compound is activated with N-hydroxy succinimide and carbodiimide and the thus-obtained mixture is directly coupled to the carrier protein.

DESCRIPTION OF THE INVENTION

It has now been found that conjugates of transferrin, albumin and polyethylene glycol, consisting of transferrin, albumin and polyethylene glycol, with a mass of between 5000 and 200000 Da and, at least, one cytostatic compound derivatized through compounds of maleinimide or N-hydroxysuccinimide, have a tumor-inhibiting effectiveness which is equal or higher than that of the cytostatic compound. Suitable for the production of these conjugates of protein or polymer are cytostatic compounds such as the anthracyclines, doxorubicin, daunorubicin, epirubicin, idarubicin and mitoxandrone, the alkylates, chloroambucil and melphalan, the antimetabolites, methotrexate, 5-fluorouracyl, 5'-desoxy-5-fluorouridine and thioguanine, the taxoides, paclitaxel and docetaxel, the camptothecins, topotecan and 9-aminocamptothecin, the podophyllotoxin derivatives, etoposide, teniposide and mitopodoside, the vinca alkaloids, vinblastine, vincristine, vindesine and vinorelbine and a compound of the general I, II, III or IV:

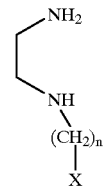

Formula I

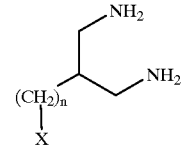

Formula II

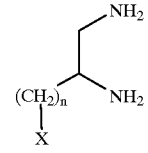

Formula III

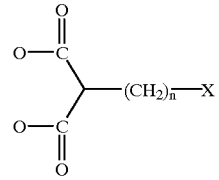

Formula IV n=0–6, X=—NH$_2$, —OH, —COOH, —O—CO—R—COR*, —NH—CO—R—COR*, wherein R is an aliphatic carbon chain with 1–6 carbon atoms or a substituted or unsubstitlted phenylene group and R* H, phenyl, alkyl with 1–6 carbon, and the amine functions are provided with a protective group such as the tert.-butyloxycarbonyl protective group, which were derivatized with a compound of maleinimide or N-hydroxysuccinimide. In doing so, the cytostatic compounds are, as a rule, reacted with a maleinimide compound or N-hiydroxysuccinimide compound which has at least one functional group which is suitable for binding to the cytostatic, such as an amino, hydroxy, carbonic acid, carbonic acid chloride, sulfonic acid, sulfonic acid chloride, acid hydracide, or hydrazino, oxycarbonyl chloride, aldehyde or keto group, so that maleinimide derivatives or N-hydroxysucciniimide ester derivatives of cytostatic compounds are prepared, wherein the chemical linkage between the maleinimide compound and cytostatic compound occurs through an amide, ester, imine, hydrazone, carboxyl hydrazone, oxycarbonyl, acetal or ketal bond. In the maleinimide or N-hydroxysuccinimide compounds which are obtained from the compounds of the formulas I–IV, the cytostatic cis-configured platinum unit is introduced subsequently, that is, the corresponding platinum (II)-complexes are obtained, after removal of the protective group, either through reaction with a tetrachloroplatinate salt or with cis-$[PtA_2B]$ (A=halogen, B=$(NH_3)_2$, ethylene diamine, propane diamine, 1,2-diaminocyclohexane).

Through reacting the derivatized cytostatic compounds with native or thiolated transferrin or albumin or with hetero- or homobifunctional PEGs with a mass of between 5000 and 200 000 Da—Overview 1:

Overview 1

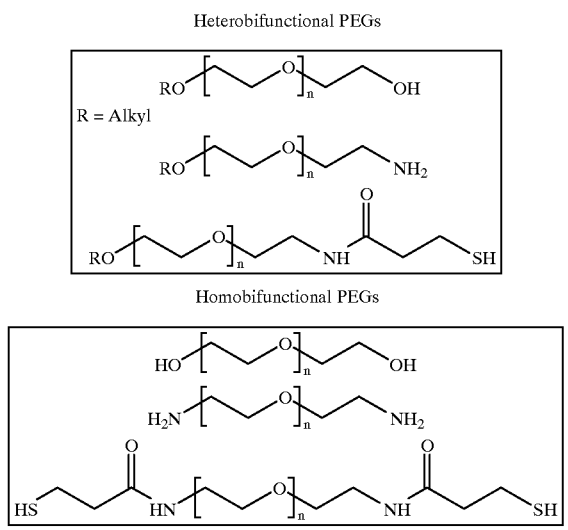

conjugates of proteins or polymers are prepared which are produced simply and effectively, having a high purity, have an excellent water-solubility in comparison to several of the original cytostatic compounds, are stable formulations in a physiologic buffer and which have an in vitro anti-proliferation effectiveness against human tumor cells which is equal to or better than that of the unbound cytostatics. Furthermore, the conjugates exhibit a equal good or improved anti-tumor effectiveness in vivo and an improved tolerability. The conjugates of protein or polyethylene glycol realized through such couplings, which are very suitable for a selective treatment of cancer diseases, are object of the invention and are described in the following.

The method for the synthesis of conjugates of protein or polyethylene glycol occurs in the conjugates with maleinimide derivatives in four steps (Steps 1 to 4), in the conjugates with N-hydrosuccinimide ester derivatives in three steps (Steps 1, 2 and 4):

Step 1: Synthesis of maleinimide or N-hydroxysuccinimide compounds
Step 2: Synthesis of maleinimide derivatives or N-hydroxysuccinimide ester derivatives of cytostatic compounds
Step 3: Thiolation of the carrier protein
Step 4: Coupling of the cytostatic compound obtained in Step 2 to native or thiolated carrier protein or to a PEG shown in Overview 1.

Step 1: Synthesis of maleinimide or N-hydroxysuccinimide Compounds

The maleinimide compounds arc generally produced according to one of the following two methods:

In the first method, maleic acid anhydride is reacted with an aliphatic amino compound $H_2N$—R—Y, wherein R is an aliphatic C-chain with 1–6 carbon atoms or a substituted or unsubstituted benzyl group and Y=—OH, —COOH, —$SO_3H$, —$CH(OC_2H_5)_2$, R* —C=O, R*=phenyl or alkyl group with 1 to 6 carbon atoms, to yield the corresponding maleaminic acid and subsequently with triethylamine ($Et_3N$) in an amount of up to two equivalents in non-aqueous toluol under azeotropic removal of the water obtained to yield the corresponding maleinimide compound. The further derivatization of the Y group occurs by reacting the —COOH or the —$SO_3H$ group with oxalyl chloride or thionyl chloride to yield the corresponding acid chlorides, by reacting the hydroxyl group with bis-(trichloromethyl)-carbonate to yield the corresponding oxycarbonyl chlorides, by reacting the acetal group —$CH(OC_2H_5)_2$ to yield the corresponding aldehyde with the help of acid-catalytic cleavage such as, for example, through p-toluol sulfonic acid, sulfuric acid or acidic silica gel, and by reacting acid chloride with N-(tert.-butoxycarbonyl)-alcohol amine or N-(tert.-butoxycarbonyl)-alcohol hydrazine and subsequent cleavage with trifluoro acetic acid or hydrogen chloride (HCl) in ether, tetrahydrofuran (THF) or dioxan yielding the corresponding amino or hydrazino compounds, respectively.

In the second method, maleic acid anhydride is reacted with an aromatic amino compound $H_2N$—R—Y, wherein R is a substituted or unsubstituted phenylene group and Y=—OH, —COOH, —$SO_3H$, R*—C=O, R*=phenyl or alkyl group with 1 to 6 carbon atoms, to yield the corresponding maleaminic acid and subsequently with acetic acid anhydride and anhydrous sodium acetate to yield the corresponding maleinimide compound. The further derivatization of the group Y occurs by reacting the —COOH or the —$SO_3H$ group with oxalyl chloride or thionyl chloride to yield the corresponding acid chlorides, by reacting the hydroxyl group with bis-(trichloromethyl)-carbonate to yield the corresponding oxycarbonyl chlorides, by reacting the acid chloride to yield the corresponding aldehydes with the help of $LiAl[OC(CH_3)_3]_3H$ in THF, by reacting the acid chloride in THF or ethyl acetate with t-buytlcarbazate and subsequent cleavage with trifluoroacetic acid or HCl in ether, THF or dioxan to yield the corresponding acid hydrazides and by reacting the acid chlorides with N-(tert.-butoxycarbonyl)-alcohol amine or N-(tert.-butoxycarbonyl)-alcohol hydrazine and subsequent cleavage with trifluoroacetic acid or HCL in ether, THF or dioxan to yield the corresponding amino or hydrazino compounds.

The maleinimide compounds of the general formulas VI and VII are produced by reacting the maleinimide compounds obtained in the above-mentioned methods, in which Y is —CO—$NHNH_2$ or —COR* with n=1–6 and R*=H, phenyl, alkyl with 1–6 carbon atoms, with carbonyl compounds of the general formula O=CR*—R—Y or with acid hydrazide of the general formula Y—R—R*CO—NH—$NH_2$ in anhydrous THF, methanol or ethanol with the optional addition of toluene-p-sulfonic acid or trifluoroacetic acid. A further derivatization of group Y occurs by reacting the COOH— or the SO$_3$H group with oxalylchloride or with thionyl chloride to yield the corresponding acid chlorides, by reacting the hydroxy group with bis-(trichloromethyl)-carbonate to yield the corresponding oxycarbonyl chlorides.

The bismaleinimide compounds of the general formula XI, wherein two maleinimide compounds are connected by a group Z, which represents a diaminoalkane, dihydroxyalkane, dihydrazinoalkane or carboxylic acid dihydrazide compound, so that two maleinimide compounds are connected with one another via two amide, ester, imine, hydrazone or carboxylhydrazone bonds, are produced from the above-mentioned maleinimide compounds, wherein the synthesis of the compounds connected by the amine bonds occurs by reacting the acid chloride of the maleinimide compounds with diaminoalkane compounds NH$_2$—(CH$_2$)$_n$—NH$_2$, n=2–12, in THF or ethyl acetate with the optional addition of Et$_3$N, the synthesis of the compounds connected by an ester bond by reacting the acid chloride of the maleinimide compounds with dihydroxy compounds HO—(CH$_2$)$_n$—OH—, n=2–12, in THF or or ethyl acetate with the optional addition of Et$_3$N, the synthesis of the compounds connected by an imine bond by reacting the aldehydes or ketones of the maleinimide compounds with diaminoalkane compounds NH$_2$—(CH$_2$)$_n$—NH$_2$, n=2–12, in anhydrous THF, methanol or ethanol with the addition of toluene-p-sulfonic acid or trifluoroacetic acid and the synthesis of the compounds connected by a hydrazone or carboxyl hydrazone bond occurs by reacting the aldehydes or ketones of the maleinimide compounds with dihydrazinoalkane compounds NH$_2$—NH—(CH$_2$)$_n$—NH—NH$_2$ or carboxylic acid dihydrazines H$_2$N—NH—CO—(CH$_2$)$_n$—CO—NH—NH$_2$, n=2–12, in anhydrous THF, methanol or ethanol with the addition of toluene-p-sulfonic acid or trifluoroacetic acid.

The N-hydroxysuccinimide compounds are produced in general by reacting N-hydroxysuccinimide with Y—R—COOH or with Y—R—COCl, wherein R is a substituted or unsubstituted phenylene group, Y=—OH, —NH$_2$, —COO—(CH$_2$)$_n$—OH, —CONH—(CH$_2$)$_n$NHBOC, —NHNHBOC, —COO—(CH$_2$)$_n$—NHNHBOC, —SO$_3$H, —SO$_2$—NHNHBOC, —CHO, —COR*, —CO—NHNHBOC with n=1–6 and R*=H, phenyl, alkyl with 1–6 carbon atoms and BOC is the tert.-butyloxycarbonyl protective group, to yield the corresponding N-hydroxysuccinimide ester compound. In so doing, the reaction starting with Y—R—COOH is preformed in anhydrous solvent, preferably dichloromethane, acetonitril or THF with the addition of dimethylaminopyridine (DMAP) and a condensation agent, as a rule, N,N'-dicyclohexylcarbodiimide (DCC) or N-cyclohexyl-N'-(2-morpholinoethyl)-carbodiimide metho-p-toluol sulfonate (CMC), to yield the corresponding succinimide ester derivatives. If the acid chloride Y—R—COCl, which is obtained through chlorination with acid halogenation reagents such as, for example, with oxalylchloride or thionyl chloride, is employed, then the reaction with N-hydroxysuccinimide occurs preferably in anhydrous THF, acetonitril or ethyl acetate.

The BOC protective group can subsequently be removed with trifluoroacetic acid or HCl in ether or dioxan, so that the corresponding amino or hydrazino compounds as well as the acid hydrazides are obtained as trifluoroacetate or hydrochlorides. A further derivatization of group Y occurs by reacting the hydroxy group with bis-(trichloromethyl)-carbonate to yield the corresponding oxycarbonyl chlorides. N-Hydroxysuccinimide compounds of the general formulas IX and X are produced by reacting the hydroxysuccinimide compounds obtained in the above-mentioned methods, in which Y is —CO—NHNH$_2$ or —COR* with n=1–6 and R*=H, phenyl, alkyl with 1–6 carbon atoms, with carbonyl compounds of the general formula O=CR*—R—Y or with acid hydrazides of the general formula Y—R—R*CO—NH—NH$_2$ in anhydrous THF, methanol or ethanol with the optional addition of toluene-p-sulfonic acid or trifluoroacetic acid. The further derivatization of group Y occurs by reacting the COOH or the SO$_3$H group with oxalylchloride or with thionyl chloride to yield the corresponding acid chlorides, by reacting the hydroxy group with bis-(trichloromethyl)-carbonate to yield the corresponding oxycarbonyl chlorides.

The isolation of the above-mentioned maleinimide and N-hydroxysuccinimide ester compounds occurs either through crystallization, through silica gel column chromotography or through preparative HPLC or LPLC on a diol column, as is described in the examples below.

Step 2: Maleinimide Derivatives or N-hydroxysuccinimide Derivatives of Cytostatic Compounds Suitable for the reaction with the maleinimide and N-hydroxysuccinimide compounds obtained in Step 1 are the cytostatic compounds mentioned in claims 1 to 3. These cytostatic compounds are reacted with the maleinimide and N-hydroxysuccinimide ester compounds described in Step 1, so that the maleinimide derivatives and N-hydroxysuccinimide ester derivatives of cytostatic compounds are provided, wherein the chemical linkage between maleinimide compound or N-hydroxysuccinimide ester compound and cytostatic compound occurs through an amide, ester, imine, hydrazone, carboxyl hydrazone, acetal or ketal bond.

In the case of the anthracyclines, doxorubicin, daunorubicin, epirubicin or idarubicin, the synthesis in detail through the reaction with acids or acid chlorides, listed in Step 1, of maleinimide or N-hydroxysuccinimide of formulas V to X to yield the corresponding anthracycline-maleinimide derivatives or corresponding anthracycline-hydroxysuccinimide derivatives in a solvent, preferably dimethylformamide (DMF) or THF with the optional addition of a tertiary base, as a rule, Et$_3$N, or with the optional addition of DMAP and a condensation agent, as a rule, DCC or CMC, wherein the coupling occurs via the 3'-NH$_2$ group of the amino sugar of anthracycline as amide an bond, or through reaction with the aldehydes or ketones of maleinimide or N-hydroxysuccinimide compounds listed in Step 1 in a solvent, preferably DMF, methanol or ethanol, with the optional addition of an acid, as a rule, toluene-p-sulfonic acid or trifluoroacetic acid, wherein the coupling occurs via the 3'-NH$_2$ group of the amino sugar of anthracycline as an imine bond, or through the reaction with the amines of maleinimide or N-hydroxysuccinimide compounds listed in Step 1 in a solvent, preferably DMF, methanol or ethanol, with the addition of an acid, as a rule, toluene-p-sulfonic acid or trifluoroacetic acid, wherein the coupling occurs via the C$_{13}$-keto position of the anthracycline as an imine bond, or through the reaction with the acid hydrazides of maleinimide or N-hydroxysuccinimide compounds listed in Step 1 in a solvent, preferably DMF, methanol or ethanol, with the addition of an acid, as a rule, toluene-p-sulfonic acid or trifluoroacetic acid, wherein the coupling occurs via the C$_{13}$-keto position of the anthracycline as a carboxyl or sulfonyl hydrazone bond.

In the case of mitoxandrone, the synthesis is performed in detail through reaction with the acids or acid chlorides of maleinimide or N-hydroxysuccinimide compounds, listed in Step 1, of formulas V to X to yield the corresponding mitoxandron-maleinimide derivatives or mitoxandron-hydroxysuccinimide derivatives in a solvent, preferably DMF or THF with the optional addition of a tertiary base, as a rule, Et$_3$N, or with the optional addition of DMAP and a condensation agent, as a rule, DCC or CMC, wherein the coupling occurs via, at least, one of the aliphatic HO-groups of the mitoxandron as an ester bond, or through reaction with the aldehydes or ketones of maleinimide or N-hydroxysuccinimide compounds listed in Step 1 in a solvent, preferably THF, methanol or ethanol with the optional addition of an acid, as a rule, trifluoroacetic acid or toluene-p-sulfonic acid, wherein the coupling occurs via, at least, one of the aliphatic HO-groups of the mitoxandron as an acetal or ketal bond.

In the case of the alkylating agents, chloroambucil and melphalan, the synthesis is performed in detail through reaction of chloroambucil or melphalan with the hydroxy compounds of maleinimide or N-hydroxysucciniimide compounds listed in Step 1 in a solvent, preferably DMF, dichloromethane or THF with the addition of DMAP and a condensation agent, as a rule, DCC or CMC, to yield the corresponding chloroambucil or melphalan-maleinimide derivatives or chloroambucil or melphalan-hydroxysuccinimide derivatives, respectively, wherein the coupling occurs via the COOH group of chloroambucil or melphalan as an ester bond, or through reaction of chloroambucil or melphalan, respectively, with acid halogenation reagents such as oxalylchloride or thionyl chloride, to yield the corresponding acid chlorides and subsequent reaction of acid chlorides in THF or ethyl acetate with t-alkylcarbazates, as a rule, tert.-butylcarbazates, or with optional addition of a tertiary base, as a rule, Et$_3$N, or through reaction of chloroambucil or melphalan in DMF, THF or ethyl acetate with t-alkylcarbazates, as a rule, DCC or CMC, and subsequent cleavage of the thus-obtained products with acids, as a rule, trifluoroacetic acid or HCl in ether, THF or dioxan, to yield the corresponding acid hydrazides of chloroambucil or melphalan, respectively, which, in turn, are reacted with one of the aldehydes or ketones, listed in Step 1, of maleinimide or N-hydroxysuccinimide compounds in a solvent, preferably DMF, methanol or ethanol with the addition of an acid, as a rule, trifluoroacetic acid or toluene-p-sulfonic acid, to yield the corresponding maleinimide or N-hydroxysuccinimide carboxyl hydrazone derivatives of chloroambucil or melphalan, respectively.

In the case of 5-fluorouracil, the synthesis occurs in detail through reaction with the acid chlorides, listed in Step 1, of the maleinimide or N-hydroxysuccinimide compounds to yield the corresponding malcinimide or N-hydroxysuccinimide derivatives of 5-fluorouracil in a solvent, preferably THF, with the optional addition of a tertiary base, as a rule, Et$_3$N, wherein the coupling occurs via the $^1$N- or $^3$N-position of 5-fluorouracil as an acid amide bond, or through the reaction with the oxycarbonyl chlorides, listed in Step 1, of the maleinimide or N-hydroxysuccinimide compounds to yield the corresponding maleinimide or N-hydroxysuccinimide derivatives of 5-fluorouracil in a solvent, preferably THF, with the optional addition of a tertiary base, as a rule, Et$_3$N, wherein the coupling occurs via the $^1$N- or $^3$N-position of 5-fluorouracil as an oxycarbonyl bond.

or through the reaction of 5-fluorouracil with formaldehyde and the carboxylic acids and sulfonic acids, listed in Step 1, to yield the corresponding maleinimide or N-hydroxysuccinimide derivatives of 5-fluorouracil in a solvent, preferably dichloromethane or THF, with the addition of DMAP and a condensation agent, as a rule, DCC or CMC, wherein the coupling occurs via the $^1$N- or $^3$N-position of 5-fluorouracil as a carbamoyloxymethyl bond.

In the case of 5'-desoxy-5-fluorouridine, the synthesis is performed in detail through reaction with the acid chlorides, listed in Step 1, of the maleinimide or N-hydroxysuccinimide compounds of formulas V to X to yield the corresponding maleinimide or N-hydroxysuccinimide derivatives of 5'-desoxy-5-fluorouridine in a solvent, preferably THF, with the optional addition of a tertiary base, as a rule, Et$_3$N, wherein the coupling occurs via the 2'-HO or 3'-HO group of 5'-desoxy-5-fluorouridine as an ester bond, or through the reaction with the aldehydes or ketones, listed in Step 1, of the maleinimide or N-hydroxysuccinimide compounds in a solvent, preferably THF, methanol or ethanol, with the addition of an acid, as a rule, trifluoroacetic acid or toluene-p-sulfonic acid, wherein the coupling occurs via the 2'-HO and/or 3'-HO group of 5'-desoxy-5-fluorouridine as an acetal or ketal bond.

In the case of thioguanine, the synthesis is performed in detail through the reaction with the acid chlorides, listed in Step 1, of the maleinimide or N-hydroxysuccinimide compounds of formulas V to X to yield the corresponding maleinimide or N-hydroxysuccinimide derivatives of thioguanine in a solvent, preferably DMF, with the optional addition of a tertiary base, as a rule, Et$_3$N, wherein the coupling occurs via the H$_2$N group of thioguanine as an amide bond, or through the reaction with the aldehydes or ketones, listed in Step 1, of the malcinimide or N-hydroxysuccinimide compounds in a solvent, preferably DMF, methanol or ethanol, with the addition of an acid, as a rule, trifluoroacetic acid or toluene-p-sulfonic acid, wherein the coupling occurs via the H$_2$N group of thioguanine as an imine bond.

In the case of methotrexate, the synthesis is performed in detail through the reaction of methotrexate with the hydroxy or amino compounds of maleinimide or N-hydroxysuccinimide compounds, listed in Step 1, in a solvent, preferably DMF or dimethylsulfoxide with the addition of DMAP and a condensation agent, as a rule, DCC or CMC, to yield the corresponding methotrexate-maleinimide derivatives or methotrexate-hydroxysuccinimide derivatives, respectively, wherein the coupling occurs either via the α-COOH group or γ-COOH group or via both COOH groups of methotrexate as an ester or amide bond, or through the reaction of methotrexate with alkylcarbazates, as a rule, t-butylcarbazate, in a solvent, preferably DMF or dimethyl sulfoxide with the addition of DMAP and a condensation agent, as a rule, DCC or CMC, and subsequent cleavage with acids, as a rule, trifluoroacetic acid or HCl in ether, THF or dioxan, to yield the corresponding acid hydrazides of methotrexate, wherein the acid hydrazide group was introduced at either the α-COOH group or γ-COOH group or at both COOH groups of methotrexate, and the thus-obtained acid hydrazide derivatives of methotrexate are reacted now with one of the aldehydes or ketones, listed is Step 1, of the N-hydroxysuccinimide compounds in a solvent, preferably DMF, methanol, THF or ethanol, with the addition of an acid, as a rule, trifluoroacetic acid or toluene-p-sulfonic acid, to yield the corresponding N-hydroxysuccinimide carboxylhydrazone derivatives of methotrexate.

In the case of the taxoides, paclitaxel and docetaxel, the synthesis is performed in detail through the reaction with the acids or acid chlorides, listed in Step 1, of maleinimide or N-hydroxysuccinimide compounds of formulas V to X to yield the corresponding taxoid-maleinimide derivatives or taxoid-hydroxysuccinimide derivatives in a solvent, preferably DMF or THF with the optional addition of a tertiary base, $Et_3N$, or with the optional addition of DMAP and a condensation agent, as a rule, DCC or CMC, wherein the coupling occurs via the $C_7$— or $C_{10}$—OH group of the taxoid as an ester bond, or through the reaction with the amines or hydrazines, listed in Step 1, of the maleinimide or N-hydroxysuccinimide compounds in a solvent, preferably DMF, methanol or ethanol, with the addition of an acid, as a rule, toluene-p-sulfonic acid or trifluoroacetic acid, wherein the coupling occurs via the $C_9$-keto position of the taxoid as an imine or hydrazone bond, or through the reaction with the acid hydrazides, listed in Step 1, of the maleinimide or N-hiydroxysuccinimide compounds in a solution, preferably DMF, methanol or ethanol, with the addition of an acid, as a rule, toluene-p-sulfonic acid or trifluoroacetic acid, wherein the coupling occurs via the $C_9$-keto position of the taxoid as a carboxyl or sulfonyl hydrazone bond.

In the case of the camptothecines, topotecan or 9-aminocamptothecine, the synthesis is performed in detail through the reaction with the acids or acid chlorides, listed in Step 1, of the malcinimide or N-hiydroxysuccinimide compounds of formulas V to X to yield the corresponding taxoid maleinimide derivatives or taxoid-hydroxysuccinimide derivatives in a solvent, preferably DMF or THF with the optional addition of a tertiary base, $Et_3N$, or with the optional addition of DMAP and a condensation agent, as a rule, DCC or CMC, wherein the coupling occurs via the $C_{10}$—OH group of the topotecan as an ester bond or via the $C_9$—$NH_2$ group of the 9-aminocamptothecin as an amide bond, or through the reaction of 9-aminocamptothecin with the aldehydes or ketones, listed in Step 1, of of the maleinimide or N-hydroxysuccinimide compounds in a solution, preferably DMF, methanol or ethanol with the optional addition of an acid, as a rule, toluene-p-sulfonic acid or trifluoroacetic acid, wherein the coupling occurs via the $C_9$—$NH_2$ group as an imine bond.

In the case of the podophyllotoxin derivatives, etoposide, teniposide and mitopodozide, the synthesis is performed in detail through reaction with the acids or acid chlorides, listed in Step 1, of maleinimide or N-hydroxysuccinimide compounds of formulas V to X to yield the corresponding taxoid-maleinimide derivatives or taxoid-hydroxysuccinimide derivatives in a solvent, preferably DMF, dichloromethane or THF with the optional addition of a tertiary base, as a rule, $Et_3N$, or with the optional addition of DMAP and a condensation agent, as a rule, DCC or CMC, wherein the coupling occurs via one of the aliphatic HO-groups of the podophyllotoxin derivative as an ester bond.

In the case of the vinca alkaloids, vinblastine, vincristine, vindesine and vinorelbine, the synthesis occurs in detail through the reaction with the acids or acid chlorides, listed in Step 1, of maleinimide or N-hydroxysuccinimide compounds of formulas V to X to yield the corresponding taxoid-maleinimide derivatives or taxoid-hydroxysuccinimide derivatives in a solvent, preferably DMF, dichloromethane or THF with the optional addition of a tertiary base, as a rule, $Et_3N$, or with the optional addition of DMAP and a condensation agent, as a rule, DCC or CMC, wherein the coupling occurs via one of the aliphatic HO-groups of the vinca alkaloid as an ester bond.

In the case of maleinimide or N-hydroxysuccinimide derivatives of the cis-configured platinum(II)-complexes, the synthesis occurs in detail through the reaction of the corresponding amino compounds $H_2N$—$CH_2CH_2$—NH—$(CH_2)_n$—X, $(H_2N$—$CH_2)_2CH$—$(CH_2)_n$—X or $H_2N$—$CH_2CH(NH_2)$—$(CH_2)_n$—X (general formulas I, II and III), wherein one or two of the primary or secondary amino groups has been protected with a BOC group (reaction with bis-tert.-butyloxy carbonyl anhydride) and X is —$NH_2$ or —OH, with the acids or acid chlorides, listed in Step 1, of maleinimide or N-hydroxysuccinimide compounds of the general formulas V–X in a solvent, preferably THF or ethyl acetate, with the optional addition of a tertiary base, as a rule, $Et_3N$, or with the optional addition of DMAP and a condensation agent, as a rule, DCC or CMC, to yield the corresponding BOC-protected maleinimide or hydroxysuccinimide derivatives which then are converted by means of trifluoroacetic acid or HCl in ether, THF or dioxan through cleavage-off of the BOC group into the corresponding trifluoroacetate or hydrochloride and finally through reaction with a tetrachloro-platinate(II) salt, preferably potassium tetrachloro-platinate(II), in water, salt buffers, DMF, DMF/water mixtures, THF/water mixtures or DMF/methanol mixtures, into the corresponding platinum(II)-complexes, wherein the coupling occurs via the terminal HO group as an ester bond or via the terminal $H_2N$ group as an acid amide bond, or through the reaction of the corresponding amino compounds $H_2N$—$CH_2CH_2$—NH—$(CH_2)_n$—X, $(H_2N$—$CH_2)_2CH$—$(CH_2)_n$—X or $H_2N$—$CH_2CH(NH_2)$—$(CH_2)_n$—X (general formulas I, II and III), wherein one or two of the primary or secondary amino groups has been protected with a BOC group (reaction with bis-tert.-butyloxy carbonyl anhydride) and X is —$NH$, or —OH, with compounds of the type HOOC—R—COCR* or ClOC—R—COCR* (R is an aliphatic carbon chain with 1–6 carbon atoms or a substituted or unsubstituted phenylene group, and R* is H, phenyl, alkyl with 1–6 carbon atoms) in a solvent, preferably THF or ethyl acetate, with the optional addition of a tertiary base, as a rule, $Et_3N$, or with the optional addition of DMAP and a condensation agent, as a rule, DCC or CMC, to yield the corresponding BOC-protected malcinimide or hydroxysuccinimide derivatives which now have a further carbonyl function which, in the following, are reacted with the amines, acid hydrazides or hydrazines, listed in Step 1, of the maleinimide or N-hydroxysuccinimide compounds in a solvent, preferably DMF, methanol or ethanol, with the addition of acid, as a rule, toluene-p-sulfonic acid or trifluoroacetic acid, to yield the corresponding imine, carboxylhydrazone or hydrazone derivatives, which then again are converted by means of trifluoroacetic acid or HCl in ether, THF or dioxan through cleavage-off of the BOC group into the corresponding trifluoroacetate or hydrochloride and finally through reaction with a tetrachloro-platinate(II) salt, preferably potassium tetrachloro-platinate(II), in water, salt buffers, DMF, DMF/water mixtures, THF/water mixtures or DMF/methanol mixtures, into the corresponding platinum(II)-complexes, or through the reaction of the corresponding amino compounds $H_2N$—$CH_2CH_2$—NH—$(CH_2)_n$—X, $(H_2N$—$CH_2)_2CH$—$(CH_2)_n$—X or $H_2N$—$CH_2CH(NH_2)$—$(CH_2)_n$—X (general formulas I, II and III), wherein one or two of the primary or secondary amino groups has been protected with a BOC group (reaction with bis-tert.-butyloxy carbonyl anhydride) and X is COOH or this carbonyl group was converted using acid halogenation reagents such as thionyl chloride or oxalyl chloride into the acid chloride, with compounds of the type HOR—COCR* or $H_2N$—R—COCR* (R is an aliphatic carbon chain with 1–6 carbon atoms or a substituted or unsubstituted phenylene group, and R* is H, phenyl, alkyl with 1–6 carbon atoms) in a solvent, preferably THF or ethyl acetate, with the optional addition of a tertiary base, as a rule, $Et_3N$, or with the optional addition of DMAP and a condensation agent, as a rule, DCC or CMC, to yield the corresponding BOC-protected maleinimide or hydroxysuccinimide derivatives which now have a further carbonyl function which, in the following, are reacted with the amines, acid hydrazides or hydrazines, listed in Step 1, of the maleinimide or N-hydroxysuccinimide compounds in a solvent, preferably DMF, methanol or ethanol, with the addition of acid, as a rule, toluene-p-sulfonic acid or trifluoroacetic acid, to yield the corresponding imine, carboxylhydrazone or hydrazone derivatives, which then again are converted by means of trifluoroacetic acid or HCl in ether, THF or dioxan through cleavage-off of the BOC group into the corresponding trifluoroacetate or hydrochloride and finally through reaction with a tetrachloro-platinate(II) salt, preferably potassium tetrachloro-platinate(II), in water, salt buffers, DMF, DMF/water mixtures, THF/water mixtures or DMF/methanol mixtures, into the corresponding platinum(II)-complexes.

In the case of maleinimide or N-hydroxysuccinimide derivatives with malonic acid derivatives of the general formula IV $(HOOC)_2$—CH—$(CH_2)_n$—X to the cis-configured platinum(II)-complexes, the synthesis occurs analogous to the above-described complexes, wherein the platinum(II)-complexes are obtained by reacting the maleinimide or N-hydroxysuccinimide derivatives with malonic acid derivatives with cis-$[PtA_2B]$ (A=halogen, preferably Cl or J, B=$(NH_3)_2$, ethylene diamine, propane diamine, 1, 2-diaminocyclohexane) to yield the corresponding platinum (II)-complexes in a solvent, such as water salt buffers. DMF, DMF/water mixtures, THF/water mixtures or DMF/methanol mixtures with the addition of a hydroxide solution, preferably aqueous KOH. The reaction can optionally be carried out in the presence of silver nitrate ($AgNO_3$) or silver sulfate ($Ag_2SO_4$). The platinum complex is obtained through crystallization or through addition of a solvent, preferably diethylether or THF.

The isolation of the above-mentioned maleinimide or N-hydroxysuccinimide cytostatic compounds, respectively, occurs either through crystallization, through silica gel column chromotography or through preparative HPLC or LPLC on a reverse-phase (C8 or C18) or diol column, as is described in the examples below.

Step 3: Thiolation of the Carrier Protein

Sulfohydryl groups (HS groups) are introduced through reaction of the carrier protein with a thiolation reagent, preferably iminothiolan, into human serum transferrin and serum albumin. The thiolation occurs in a salt buffer, as a rule, in 0.1 M sodium borate, 0.15 M NaCl, 0.001 M EDTA—pH=8.0, with an excess of thiolation reagent (2- to 100-fold excess) and subsequent gel filtration (for example, Sephadex® G 10 of G25) with a salt buffer such as 0.025 M sodium borate, 0.15 M NaCl—pH 6.014 7.5 or 0.004 M phosphate, 0.15 M NaCl—pH 6.0–7.5. The concentration of protein after completed gel filtration is determined through the extinction coefficient at 280 nm and is, as a rule, in the range of between $1.0 \times 10^{-4}$ and $5.0 \times 10^{-3}$ M. The number of the introduced HS groups is determined with Ellmanin's reagent at 412 nm. Through variation of the reaction conditions, 1 to 30 HS groups can be introduced on the average. The thiolated transferrin or albumin solution is employed directly for the synthesis of the conjugates.

Step 4: Coupling of the Cytostatic Maleinimide or N-hydroxysuccinimide Compounds to the Native or Thiolated Carrier Protein or to a Polyethylene glycol Shown in Overview 1

For the coupling of the cytostatic maleinimide or N-hydroxysuccinimide compounds to PEGs, PEGs are employed which have one or two HO—, HS— or $H_2N$ groups and a mass of between 5,000 and 200,000 Da, preferably between 20,000 and 70,000 Da. Corresponding compounds are not commercially available. In the following, polyethylene glycols having one or two HS groups are shortened with HS-PEG or HS-PEG-SH, and the PEGs having one or two $H_2N$ groups are shortened with $H_2N$-PEG or $H_2N$-PEG-$NH_2$.

Coupling of the cytostatic, maleinimide derivatives to the thiolated carrier protein or to HS-PEG, HS-PEG-SH, $H_2N$-PEG or $H_2N$-PEG-$NH_2$: The cytostatic maleinimide derivatives (see Step 2) are reacted with thiolated transferrin, albumin (see Step 3), HS-PEG, HS-PEG-SH, $H_2N$-PEG or $H_2N$-PEG-$NH_2$ at room temperature. In so doing, to the thiolated protein, HS-PEG, HS-PEG-SH, $H_2N$-PEG or $H_2N$-PEG-$NH_2$, which is present in a degassed salt buffer such as 0.025 M sodium borate, 0.15 M NaCl—pH 6.0 to 7.5 or 0.004 M phosphate, 0.15 M NaCl—pH 6.0 to 7.5, an approximately 1.1- to 10-fold excess of the cytostatic maleinimide derivative is added (in terms of the number of available HS groups in the protein or PEG), dissolved in a minimal amount of solvent, as a rule, DMF, dimethylsulfoxide, water, ethanol, methanol, acetonitril or THF (approximately 1 to 10% of the volume of the thiolated sample). After approximately 5 to 120 minutes, the solution is centrifuged, and the formed protein conjugate or PEG conjugate is separated off through subsequent gel filtration (for example, Sephadex® G10, G25 or LH20) in a degassed salt buffer such as 0.025 M sodium borate, 0.15 M NaCl—pH6.0–7.5, 0.004 M phosphate, 0.15 M NaCl—pH 6.0–7.5 or 0.1–0.2 M $NaHCO_3$, or in methanol or THF, from the excess cytostatic maleinimide derivative. It can be advantageous to dilute the thiolated protein solution prior to the addition of the maleinimide derivative with a salt buffer and to add the maleinimide derivative, which is dissolved in a minimal amount of solvent, and subsequently to concentrate the solution after 5–20 minutes with a customary commercial concentrator and to isolate the protein conjugate, as described above. Further, the solution of the thus-obtained protein conjugate or of the PEG conjugate can be concentrated with a customary commercial concentrator or the solvent removed under a high vacuum.

Coupling of the cylostatic N-hydroxysuccinimide derivatives to the native carrier protein or to HO-PEG, HO-PEG-OH, $H_2N$-PEG or $H_2N$-PEG-$NH_2$: The cytostatic N-hydroxysucciniimide derivatives (see Step 2) are reacted with transferrin, albumin, HO-PEG, HO-PEG-OH, $H_2N$-PEG or $H_2N$-PEG-$NH_2$ at room temperature. In so doing, to the protein, HO-PEG, HO-PEG-OH, $H_2N$-PEG or $H_2N$-PEG-$NH_2$, which is located in a degassed salt buffer such as 0.025 M sodium borate, 0.15 M NACl—pH 6.0 to 8.0 or 0.004 M phosphate, 0.15 M NaCl—pH 6.0 to 8.0, an approximately 1.1- to 50-fold excess of the cytostatic N-hydroxysuccinimide derivative is added, dissolved in a minimal amount of solvent, as a rule, DMF, dimethylsulfoxide, water, ethanol, methanol, acetonitril or THF (approximately 1 to 10% of the volume of the thiolated sample). After approximately 5 minutes to 48 hours, the solution is centrifuged, and the formed protein conjugate or PEG conjugate is separated off through subsequent gel filtration (for example, Sephadex® G10, G25 or LH20) in a degassed salt buffer such as 0.025 M sodium borate, 0.15 M NaCl—pH 6.0–7.5, 0.004 M phosphate, 0.15 M NaCl—pH 6.0–7.5 or 0.1–0.2 M $NaHCO_3$, or in methanol or THF, from the excess cytostatic N-hydroxysuccinimide derivative. The solution of the thus-obtained protein conjugate or of the PEG conjugate can be concentrated with a customary commercial concentrator or the solvent removed under a high vacuum.

The number of the cytostatic maleinimide derivatives or N-hydroxysuccinimide derivatives bound to the carrier protein or to the polyethylene glycol is specified either through a photometric concentration determination at the absorbed wavelength of the cytostatic maleinimide or N-hydroxysuccinimide derivative (typically between 220 and 600 nm) and/or through colorimetric determination which, in the case of the conjugates of chloroambucil and melphalan, is performed with the aid of the NBP test (Epstein, J., Rosenthal, R. W., Ess, R. J. *Anal. Chem.* (1955), 27, 1435–1439), in the case of the conjugates of 5-fluorouracil and 5'-desoxy-5-fluorouridine with the aid of an assay according to Habib (Habib, S. T., *Talanta* (1981), 28, 685–87) and in the case of the conjugates of the cis-configured platinum(II)-analogues with the aid of a determination according to Gonias and Pizzo (Gonias, S. L., Pizzo, S. V. *J.Biol.Chem.* (1982), 258, 5764–5769) or according to atomic absorption spectroscopy (AAS).

On the average, through the above-described way, approximately 1–30 molecules of the cytostatic compound is bound to one molecule of protein or 1–2 molecules of the cytostatic compound to one molecule of the PEGs. The purity of the protein conjugate or the PEG conjugate is checked through HPLC with the aid of an analytical column (Bio-Sil SEC 250, (300 mm×7.8 mm) from Bio-RAD, mobile phase: as a rule, 0.15 M NaCl, 0.01 M $NaH_2PO_4$, 5% of $CH_3CN$—pH 7.0 or Nucleogel® aqua-OH 40 or 60, from Macherey and Nagel, mobile phase: as a rule, 0.1 M NaCl, 0.004 M $NaH_2PO_4$, 30% methanol—pH 7.0). In so doing, the transferrin, albumin and polyethylene glycol conjugates exhibit a purity of >90%.

The protein conjugates or PEG conjugates can be stored in a dissolved form at 0–5° C., in frozen form at T=–20° C. or –78° C. Furthermore, it is possible to lyophilize the solution of the conjugate and store the lyophilisate at +5 to –78° C.

Object of the invention are also such chemoimmuno-conjugates consisting of albumin which, according to one of the claims 1 to 3, is loaded with approximately two to thirty equivalents of a cytostatic compound and is conjugated, with a protein, for example, with transferrin or with a monoclonal antibody which is directed against a tumor-associated antigen, preferably, however, with transferrin, via one of the bismaleinimide compounds mentioned in claim 3 or via an aliphatic or aromatic bismaleinimide compound. In so doing, approximately 80–90% of the thiol groups introduced into albumin with the cytostatic maleinimide derivative, dissolved in a minimal amount of solvent, as a rule, DMF, dimethylsulfoxide, ethanol, methanol, acetonitril or THF (approximately 1–10% of the volume of the thiolated sample) are reacted and, after approximately 5 to 60 minutes, a 1.5- to 20-fold excess of the bismaleinimide compound, dissolved in a minimal amount of solvent, as a rule, DMF, dimethylsulfoxide, ethanol, methanol, acetonitril or THF (approximately 1–10% of the volume of the thiolated sample) is added. After approximately 5 to 20 minutes, the solution is centrifuged, and the formed protein conjugate separated off through subsequent gel filtration (for example, Sephadex® G10 or G25) in a salt buffer, as a rule, 0.025 M sodium borate, 0.15 M NaCl—pH 6.0–7.5 or 0.004 M phosphate, 0.15 M NaCl—pH 6.0–7.5, from the cytostatic maleinimide derivative and the bismaleinimide compound. Then the thus-modified albumin conjugate is reacted with one of the proteins mentioned above which contains approximately 1.5 thiol groups on the average, and the resulting chemoimmuno-conjugate which now consists of an albumin molecule loaded with a cytostatic compound and of the above-mentioned protein, is isolated with the aid of a Superdex-200 column (company: Pharmacia) or a hydroxyl apetite column (company: Pharmacia or Bio-Rad) in a salt buffer, as a rule, 0.025 M sodium borate, 0.15 M NaCl—pH 6.5–8.0, 0.004 M phosphate, 0.15 M NaCl—pH 6.5–8.0.

It is also possible to, first, react one of the above-mentioned proteins, which contains 1.5 thiol groups on the average, with a 1.5- to 10-fold excess of the bismaleinimide compound and then to separate the formed protein conjugate through subsequent gel filtration (for example, Sephadex® G10 or G25) in a degassed salt buffer such as 0.025 M sodium borate, 0.15 M NaCl—pH 6.0–7.5, 0.004 M phosphate, 0.15 M NaCl—pH 6.0–7.5 or 0.1–0.2 M $NaHCO_3$, from the bismaleinimide compound, and then to react the thus-modified protein conjugate, which now contains 1.5 equivalents of the bismaleinimide compound on the average, with the modified albumin conjugate, wherein approximately 80–90% of the thiol groups introduced into the albumin have already been reacted with a cytostatic maleinimide derivative. The resulting chemoimmuno-conjugate which now consists of an albumin molecule loaded with a cytostatic compound and of the above-mentioned protein, is isolated with the aid of a Superdex-200 column (company: Pharmacia) or a hydroxyl apatite column (company: Pharmacia or Bio-Rad) in a degassed salt buffer, such as, 0.025 M sodium borate, 0.15 M NaCl—pH 6.0–8.0, 0.004 M phosphate, 0.15 M NaCl—pH 6.0–8.0 or 0.1–0.2 M $NaHCO_3$.

The following examples describe the invention in more detail without limiting it.

EMBODIMENTS EXAMPLES

Step 1: Synthesis of Maleinimide-and Hydroxysuccinimide Compounds p-Maleinimidobenzophenone 14.0 g (70 mmol) of p-aminobenzophenone were dissolved in 70 ml of acetone and 7.0 g (70 mmol) maleic acid anhydride, dissolved in 40 ml of acetone, were added drop-wise over a period of 15 minutes at room temperature. This set-up was stirred for 3 h at room temperature. Then the precipitation was filtered off, washed with ether and dried under a vacuum (yield: 93%). 19.3 g (65.4 mmol) of N-(p-benzophenyl)-maleic acid amide and 2.6 g (31.0 mmol) of anhydrous sodium acetate were dissolved at 55° C. in 50 ml of acetic acid anhydride and stirred at this temperature for 2 h. Subsequently, the acetic acid anhydride was removed at 60° C. under a water jet vacuum. To the residue, 300 ml of water was added and stirred for 2 h at 70° C. The precipitation precipitating during this time was suctioned off, washed with water, and dissolved and recrystallized out of acetone (yield: 94%); melting point: 150° C.; $R_f$-value: 0.70 (acetic ester/hexane 6/1); calculated: C: 73.64% H: 3.97% N: 5.05%, $C_{17}H_{11}NO_3$; found: C: 73.15% H: 3.96% N: 5.00%.

p-Maleinimidophenylacetic acid 25.0 g (166.9 mmol) of p-aminophenylacetic acid were suspended in 250 ml of methanol and while heating brought into the solution with the addition of 500 ml. 19.25 (166.9 mmol) of maleic acid anhydride were dissolved in 100 ml of acetone and, over a period of 60 minutes, added drop-wise to the solution previously cooled to 40° C. The set-up was stirred for 60 minutes at room temperature. Then the reaction mixture was concentrated to approximately 300 ml and set aside to cool at –20° C. The precipitation was suctioned off, washed with acetone and dried under a high vacuum (yield: 82%). 18.0 g (72 mmol) of N-(4-acetic acid phenyl) maleic acid amide were suspended in 2.4 liters of toluene and heated to reflux. While heating, 14.7 g (20.2 ml, 144 mmol) of triethyl amine were added and subsequently heated for 2 hours to reflux at the water separator. Then it was destined off from the formed red oil and the solvent was removed under a vacuum. The yellow residue was dissolved in 300 ml of water and set to pH=2 with 1 M HCl. The acidic solution was extracted with acetic ester (6×50 ml). The combined acetic ester phases were dried via sodium sulfate and the solvent removed under a vacuum. The product was recrystallized from acetic ester/hexane (yield: 51% yellow crystals); melting point: 158° C.; $R_f$-value: 0.45 (acetic ester/methanol 2/1); calculated: C: 62.34% H: 3.92% N: 6.09%, $C_{12}H_9NO_4$; found: C: 61.84% H: 4.43% N: 5.59%.

p-Maleinimidophenylacetic acid chloride 1.0 g (4.33 mmol) of p-maleinimidophenylacetic acid were suspended in 25 ml of dichloromethane and diluted with a 2.5-fold excess of oxalic acid dichloride (1.37 g, 945 µl; 10.82 mmol). The reaction mixture was heated to 30–40° C. with the exclusion of moisture and stirred for 15 h. Then the solvent was removed under a vacuum and dried under a high vacuum. Crystallization from toluene yielded a yellow powder (yield: 59%); melting point: 154° C.; $R_f$-value: 0.29 (acetic ester/hexane 4/1); Elementary analysis: calculated: C: 58.91% H: 3.30% N: 5.75%, Cl: 14.49%; ($C_{12}H_8NO_3Cl$) found: C: 60.61% H: 3.64% N: 5.13% Cl: 13.80%.

p-Maleinimidophenylacetic acid hydrazide.$CF_3COOH$ 3.5 g (14 mmol) of p-maleinimidophenylacetic acid chloride were dissolved together with tert.-butylcarbazate (2.87 g, 21.7 mmol) in 50 ml of anlhydrous tetrahydrofuran and stirred for 2 h at room temperature. The tetrahydrofuran was removed under a high vacuum and the residue taken up in 500 ml of acetic ester. The acetic ester phase was shaken out twice with 125 ml of water each and then dried via anlhydrous sodium sulfate. The solution was concentrated by evaporation, and dissolved and recrystallized from acetic ester/hexane. The product was suctioned off and dried under a high vacuum (yield: 90%); melting point: decomposition at 152° C.; $R_f$-value: 0.50 (tetrahydrofuran/hexane 3/1). 2.5 g (7.25 mmol) p- maleinimidophenylacetic acid hydrazino-tert.-butylcarbazate were dissolved in 12 ml of trifluoroacetic acid and stirred for 1 h at room temperature. The trifluoroacetic acid was subsequently removed under a high vacuum and the residue suspended in 50 ml of ether. The precipitate was suctioned off, washed with dry ether and dried under a high vacuum (yield: 82% yellowish powder); melting point: 1 12° C.; $R_f$-value: 0.06 (tetrahydrofuran/hexane 3/1); calculated: C: 46.80% H: 3.34% N: 11.70%; ($C_{14}H_{12}N_3O_5F_3$) found: C: 46.95% H: 3.24% N: 11.51%.

Maleinimidoacetaldehyde 91.6 g (100 ml, 689 mmol) aminoacetaldehyde diethylacetal were dissolved in 200 ml of acetic ester. Thereafter, 67.5 g (689 mmol) of maleic acid anhydride, dissolved in 200 ml of acetic acid, were added drop-wise while stirring and cooling with ice within 60 minutes. Stirring, was performed for 1 h at room temperature. Then the reaction mixture was concentrated to the half and set to cool at −20° C. After 24 h, the obtained precipitate was suctioned off under a vacuum, washed with acetic ester and ether, and subsequently dried under a high vacuum. (Yield: 90%). 30.95 g (133.8 mmol) of N-(acetaldehyde diethylacetal) maleic acid amide were dissolved in 900 ml of toluene, 14.2 g (19.6 ml, 140.5 mmol) of triethylamine were added thereto and the reaction mixture boiled for 15 h at the water separator. Thereafter, the solvent was removed under a vacuum. The remaining syrup was taken up in 350 ml of diethyl ether and extracted 3× with 50 ml of water each. The ether phase was dried over $Na_2SO_4$, the solvent removed under a vacuum and the residue purified using column chromatography (acetic ester/hexane 1/1; yield: 36% of colorless syrup); ; $R_f$-value: 0.49 (acetic ester/hexane 1/1); calculated: C: 58.15% H: 7.49% N: 6.17%; ($C_{10}H_{15}NO_4$) found: C: 58.10% H: 6.98% N: 6.35%.

20.1 o (94.3 mmol) of maleinimidoacetaldehyde diethylacetal were dissolved in 350 ml of dichloromethane and 40.2 of silica gel 60 were added while stirring. 4.0 g of 30-% sulfuric acid were added and refluxed for 60 h. Then the silica gel was filtered off and the reaction solution was extracted with 4×50 ml of water. The dichloromethane was dried over sodium sulfate and concentrated through evaporation. The residual syrup was dissolved and recrystallized from acetic ester/hexane (1:10) (yield: 15% white crystal); melting point: 68–69° C.; $R_f$-value: 0.52 (THF/hexane 3/1); calculated: C: 51.76% H: 3.62% N: 10.06%; ($C_6H_5NO_3$) found: C: 51.48% H: 4.14% N: 9.60%.

2-maleinimidoethyl chloroformate 2.0 g (14.2 mmol) 2-hydroxyethylmaleinimide were dissolved in 150 ml of absolute dichloromethane and diluted with 1.56 g (4.8 mmol) of triphosgene. After the addition of 479 mg (660 µl; 4.8 mmol) of triethylamine, the set-up was stirred for 72 h at room temperature, subsequently the solvent was removed under a vacuum and the residue was purified using column chromatography via silica gel (running medium: acetic ester/hexane 2/1; yield: 80% colorless solid); melting point: 45° C.; $R_f$-value: 0.69 (acetic ester/hexane 2/1); calculated: C: 41.25% H: 2.95% N: 6.88%, Cl: 17.41%; ($C_7H_6NO_4Cl$) found: C: 41.11% H: 3.00% N: 6.88% Cl: 16.94%.

Synthesis of Bisnialeinimide Compounds 1,4-diamino-N,N'-di-m-maleinimidobenzyl-butane 2.36 g (10 mmol) of maleinimidobenzoic acid chloride as well as 0.44 g (5 mmol) of 1,4-diaminobutane were dissolved each in 60 ml of ethyl acetate. In a three-necked flask, 40 ml of ethyl acetate were placed. While stirring at room temperature, both of the solutions were added drop-wise to synchronously over a period of 30 minutes. During the drop-wise addition, a light-yellow precipitate precipitated out. The set-up 20 was stirred for 2 h, the precipitate suctioned off and washed with diethylether. The light-yellow solid was dissolved and recrystallized out from acetone, washed with water and then again with ether and dried under a vacuum. 2.1 g (3.9 mmol, 75% of the theory) of the product were obtained as a yellow-white solid, DC: silica gel, THF/hexane 4:1, $R_f$-value: 0.30 (THF/hexane 3/1), Fp.: 221° C. (decomposition); $C_{26}H_{22}N_4O_6$(486 g/mol) calculated: C: 64.20% H: 4.53% N: 11.52% O: 19.75%; found: C: 62.57% H: 4.55% N: 10.67%.

Diacylhydrazone from adipic acid dihydrazide and m-maleinimidoacetophenone 1.0 g (4.65 mmol) m-maleinimidoacetophenone was dissolved together with 368 mg (2.11 mmol) of adipic acid dihydrazide in 40 ml of absolute methanol. To the reaction mixture was added 100 µl of trifluoroacetic acid and stirred for 15 h at room temperature. The precipitate thus precipitating out was suctioned off and washed 2× with 30 ml of methanol each as well as 4× with 50 ml of diethylether each. Then the product was dried under a vacuum; DC: silica gel, THF/hexane 4: 1, $R_f$=: 0.36, Fp.: 240° C. (decomposition); $C_{30}H_{28}N_6O_6$(568 g/mol) calculated: C: 63.38% H: 4.93% N: 14.79%; found: C: 63.18% H: 4.83% N: 15.03%.

Synthesis of N-hydroxysuccinimide Ester Compounds 4-acetophenone carboxylic acid-(N-hydroxysuccinimide)-ester 2.2 g (1.2 mmol) acetophenone-4-carboxylic acid and 1.52 g (1.3 mmol) and 20 mg of DMAP are dissolved in 40 ml of tetrahydrofuran and then 2.7 g of DCC, dissolved in 20 ml of THF, were added drop-wise while cooling within 1 h. The reaction mixture is stirred while cooling over a period of 12 h, filtered, THF removed under a vacuum, and the residue dissolved and recrystallized from acetic ester/methanol 1: 1, $R_f$=0.71, Fp.: 140° C.; $C_{13}H_{11}NO_5$(261 g/mol); calculated: C: 59.77% H: 4.21% N: 5.36%; found: C: 60.1% H: 4.2% N: 5.0%.

4-Carboxylbenzoylhydrazide 25 g (138.9 mmol) of terephthalic acid monomethylester are suspended in 200 ml of THF and heated to reflux. In the portion-wise addition of 40.5 ml (833.4 mmol, 6 eq) of hydrazine monohydrate, the product precipitates out as a white solid. The excess THF is distilled off and the residue dissolved in water. Through the addition of conc. HCl, a pH of approximately 4 is set. A white precipitate is formed which is suctioned off and washed with half-conc. HCl. The product is dried under a vacuum, and dissolved and recrystallized from methanolic caustic soda solution. Obtained are 24.84 g (138 mmol) of the product in the form of colorless crystal needles, corresponding to 99.3% of the theoretically possible yield. $C_8H_8N_2O_3$ (180 g/mol); calculated: C: 53.33% H: 4.44% N: 15.55%; found: C: 52.41% H: 4.26% N: 14.68%.

N-Tertiarybutyloxycarbonyl-4-carboxybenzoylhydrazide 20 g (0.11 mol) 4-carboxybenzoylhydrazide are suspended in 200 ml of THF and diluted with a solution of 23.98 g (0.11 mol) of bis-tert.-butyldicarbonate in 50 ml of THF. After 48 h of stirring at room temperature, the THF is removed under a vacuum, the oily residue taken up in 400 ml of ethylacetate and extracted 4 times each with 100 ml of water. After drying of the organic phase over $Na_2SO_4$, it is concentrated to half and cooled to 4° C. Colorless crystals are formed which are suctioned off and washed with diethylether. Obtained are 30.3 g (0.108 mmol) of the product, corresponding to 98.4% of the theoretically possible yield. $C_{13}H_{16}N_2O_5$ (280 g/mol) calculated: C: 55.71% H: 5.71% N: 10.00%; found: C: 56.94% H: 5.56% N: 9.79%.

N-Tertiarybutyloxycarbonyl-4-(N-hydroxysuccinimidocarbonyl)benzoylhydrazide 4 g (14.29 mmol) N-tertiarybutyloxycarbonyl-4-carboxybenzoylhydrazide are dissolved together with 3.29 g (28.6 mmol) of N-hydroxysuccinimide and 17.4 mg of DMAP in 100 ml of THF and diluted drop-wise at 4° C. with a solution of 3.23 g (15.72 mmol) of DCC. After 12 h of stirring at 4° C. and 48 h at room temperature, the solvent is removed under a vacuum, the residue dissolved in ethylacetate and extracted 10 times each with 50 ml of saturated NaCl solution. After drying of the organic phase over $Na_2SO_4$, it is concentrated to half and cooled to 4° C. Colorless needles are formed which are suctioned off and washed with a small amount of diethylether. Obtained are 5.3 g (14.09 mmol), corresponding to 98.6% of the theoretically possible yield. $C_{17}H_{18}N_3O_7$ (376 g/mol); calculated: C: 54.26% H: 4.79% N: 11.18%; found: C: 52.65% H: 5.53% N: 10.56%.

4-(N-hydroxysuccinimido)carbonyl)benzoylhydrazide trifluoroacetate 3 g (7.98 mmol) of N-tertiarybutyloxycarbonyl-4-(N-hydroxysuccinimidocarbonyl) benzoylhydrazide are diluted with 10 ml of anhydrous trifluoroacetic acid and stirred over a period of 2 h at room temperature. During rigorous stirring, 50 ml of diethylether is added. The solid formed is suctioned off and washed several times with diethylether. After drying under a vacuum, 3.0 g (7.67 mmol) of the product are obtained as a white powder, corresponding to 96.1% of the theoretically possible yield. $C_{14}H_{12}N_3O_7F_3$ (391 g/mol); calculated: C: 42.97% H: 3.07% N: 10.74%; found: C: 43.49% H: 3.42% N: 10.74%.

Step 2: Synthesis of Maleinimide and Hydroxysuccinimide Derivatives of Cytostatic Compounds Chloroambucilcarboxylic acid hydrazide Chloroambucil (1.0 g; 3.29 mmol) was dissolved in 50 ml of absolute $CH_2Cl_2$ and diluted with oxalylchloride (431 µl; 4.8 mmol) and the set-up stirred for 15 h at 30–40° C. Subsequently, the solution is concentrated through evaporation and residues of oxalylchloride removed under a high vacuum. The synthesized oxalylcarboxyl acid chloride was directly reacted further by dissolving the obtained brown syrup in 20 ml of absolute $CH_2Cl_2$ and, while stirring at room temperature, tert.-butylcarbazate (457 mg; 3.45 mmol), dissolved in 20 ml of $CH_2Cl_2$, was added drop-wise within 1 h. The set-up was stirred for 36 h, filtered off from the insoluble parts and the solution concentrated under a vacuum to approximately 3 ml. The obtained chloroambucil-tert.-butylcarbazate was brown syrup purified using a column chromatography (running medium: acetic ester/hexane 2/1; $R_f$-value: 0.52), yield: 700 mg (1.67 mmol; 51% of the theoretical value). Chloroambucil-tert.-butylcarbazate (700 mg; 1.67 mmol) was dissolved in 10 ml of tetrahydrofuran and diluted while stirring at room temperature with 10 ml of trifluoroacetic acid, stirred for 1 h and subsequently the solvent and the trifluoroacetic acid removed under a high vacuum with the formation of a light-brown solid.

Carboxylhydrazone derivative of [4-(4-bis(2-chloroethyl) aminophenyl)]butyric acid hydrazide (trifluoroacetate salt) and 4-acetophenonecarboxylic acid-(N-hydroxysuccinimide)-ester Chloroambcilcarboxylic acid hydrazide (trifluoroacetate salt; 721 mg; 1.67 mmol) was dissolved in 30 ml of tetrahydrofuran and diluted while stirring at room temperature with 4-acetophenonecarboxylic acid-(N-hydroxysuccinimide)-ester (479 mg; 1.83 mmol). After 20 minutes, the reaction solution was concentrated by evaporation. The residue was dissolved and recrystallized out from acetic ester/hexane; yield: 290 mg (0.66 mmol; 40% of the theory) light-yellow crystals; ($C_{27}H_{31}N_4O_6Cl_2$, Mr 577), calculated: C: 56.2% H: 5.4% N: 9.7%, Cl: 12.1%; found: C: 56.3% H: 5.6% N: 12.4% Cl: 11.7%.

$N^1$-(2-Maleinimidoethyloxycarbonyl)-5-fluorouracil 500 mg (3.84 mmol) 5-fluorouracil were dissolved in 100 ml of tetrahydrofuran and diluted with 505 mg (696 µl; 4.99 mmol) of triethylamine. To this solution, 1016 mg (4.99 mmol) of 2-maleinimidoethyl chloroformate, dissolved in 100 ml of tetrahydrofuran, were added drop-wise and the set-up was stirred for 15 h at room temperature. Then, the solvent was removed under the water jet vacuum and the residue purified using column chromatography (LOBAR®-column; running medium: acetic acid/hexane 1.5/1; yield: 61%); melting point: 132° C., $R_f$-value: 0.64 (diol; acetic acid/hexane 2/1); calculated: C: 44.29% H: 2.68% N: 14.09%, ($C_{11}H_8N_3O_6F$); found: C: 44.29% H: 2.68% N: 13.58%.

$N^1$-(m-Maleinimidobenzoyloxymethyl)-5-fluorouracil 1500 mg (11.55 mmol) 5-fluorouracil and 2.25 ml (25.4 mmol) of 37-% formaldehyde solution were heated to 60° C. while stirring for 2 h. Then, the water was removed under a high vacuum and the residue dissolved with the addition of 20 mg of DMAP in 80 ml of tetrahydrofuran. To this solution, 3.01 g (13.85 mmol) of m-maleinimidobenzoic acid and 2.858 g (13.85) of DCC, dissolved in 50 ml of tetrahydrofuran, were added and then stirred for 15 h at room temperature. The precipitate was filtered off and the solvent removed under a vacuum. The residue was taken up in approximately 20 ml of acetic acid and filtered off from insoluble parts. The solution was concentrated by evaporation and the residue chromatographed (1. silica gel (acetic ester/hexane 2/1); yield: 5% white powder); melting point: decomposition >250° C.; $R_f$-value: 0.32 (acetic acid/hexane 2/1); Elementary analysis calculated: C: 55.98% H: 2.92% N: 12.24%; ($C_{16}H_{10}N_3O_6F$) found: C: 55.51% H: 2.87% N: 11.72%.

3'-Aminoamide derivative of doxorubicine with p-maleinimidophenylacetic acid chloride 500 mg (0.86 mmol) doxorubicine hydrochloride were dissolved in 50 ml of absolute DMF and 1013 mg (4.30 mmol) of p-maleinimidophenylacetic acid chloride and 719 µl (522 mg; 5.16 mmol) of triethylamine were added. The solution was stirred at room temperature for 15 h. DMF was removed under a high vacuum and the residue was dissolved in 5 ml of tetrahydrofuran, filtered and purified over a silica gel column (tetrahydrofuran/hexane 3/1); 189 mg of the red product (29%); $R_f$-value: 0.26 (ethylacetate/hexane 3/1); melting point: 110° C.; ($C_{39}H_{36}N_2O_{14}$); calculated: C: 61.84% H: 4.75% N: 3.70%; found: C: 61.35% H: 5.14% N: 3.45%.

C-13-Benzoylhydrazone derivative of doxorubicine and 4-((N-hydroxysuccinimido)carbonyl)benzoylhydrazide trifluoroacetate 0.2 mmol doxorubicine hydrochloride and 1.0 mmol and 4-((N-hydroxysuccinimido)carbonyl)benzoylhydrazide trifluoroacetate salt were dissolved in 100 ml of methanol. To this solution, 100 µl of $CF_3COOH$ were added and the reaction mixture stirred for 36 h at room temperature. The solution was then concentrated to approximately 50 ml. Acetonitril was added until reaching turbidity and the suspension was cooled at −20° C. for 24 h. The product was collected by means of centrifugation, and dissolved and recrystallized from methanol/acetonitril: 276 mg; $R_f$-value (reverse phase, acetonitril/0.005 M $NaH_2PO_4$ (pH 5.0)=70/30): 0.33, melting point: >250° C. (decomposition), ($C_{39}H_{40}N_4O_{14}Cl$); calculated: C: 56.83% H: 4.86% N: 6.80% Cl 4.31%; found: C:57.04% H:5.14% N:6.55% Cl 14.12%.

The method for the production of maleinimide derivatives with cis-configured platinum(II) units is described by the following example: N—(O-(3-maleinimidobenzoyl)-2-hydroxyethyl)-2-diaminoethane dichloroplatinum(II)—four-step synthesis.

N-(2-Hydroxyethyl)-N,N'-bis-tertiarybutyloxycarbonyl-1 2-diaminoethane

To a solution of 20.8 g (200 mmol) of N-(2-hydroxyethyl)-1,2-diaminoethane in 100 ml of dichloromethane, 47.96 g (220 mmol, 0.5 eq) of bis-teitiarybutyloxycarbonylanhydride, dissolved in 200 ml of dichloromethane, were added drop-wise within 1 h at room temperature. The set-up is stirred for 12 h at room temperature, then diluted with 100 ml of diethylether and extracted with 150 ml of water. After drying of the organic phase over sodium sulfate, it is concentrated under a vacuum. The purification of the product occurs through the use of column chromatography (ethylacetate/hexane (1:1.5), $R_f$-value: (ethylacetate/hexane 1:1.5): $R_f$=0.18; yield: 30 g (98.68 mmol). Elementary analysis for $C_{14}H_{28}N_2O_5$ (304 g/mol); calculated: C: 55.26% H: 9.21% N: 9.21%; found: C: 55.50% H: 9.18% N: 9.02%.

N-(O-(3-maleinimidobenzoyl)-2-hydroxyethyl)-N,N'-bis-tertiarybutyloxycarbonyl-1,2-diaminoethane To a solution of 8 g (26.3 mmol) N-(2-hydroxyethyl)-N,N'-bis-tertiarybutyloxycarbonyl-1,2-diaminoethane in 50 ml of tetrahydrofuran and 4 ml (28.9 mmol, 1.1 eq) of triethylamine, 6.82 g (29 mmol, 1.1 eq) of maleinimidobenzoic acid chloride, dissolved in 100 ml of tetrahydrofuran, are added drop-wise at room temperature while stirring within 1 h. After stirring for a further 8 h at room temperature, according to DC, the reaction is completed. The triethylammonium chloride formed in the reaction is filtered off. After removal of the tetrahydrofuran and the excess triethylamine under a vacuum, the oil formed is purified using column chromatography (silica gel: ethyl acetate/hexane (1:1), $R_f$-value (ethyl acetate/hexane 1:1)= 0.2, yield: 9.6 g (19.1 mmol) of the product in the forM a yellow oil, corresponding to 72.6% of the theoretically possible yield. Elementary analysis for $C_{25}H_{33}N_3O_8$ (503 g/mol); calculated: C: 59.64% H: 6.56% N: 8.35%; found: C: 60.04% H: 6.77% N: 8.24%.

N-(O-(3-maleinimidobenzoyl)-2-hydroxyethyl)-1,2-diaminoethane dihydrochloride 6 g (11.93 mmol) of N-(O-(3-maleinimidobenzoyl)-2-hydroxyethyl)-N,N'-bis-tertiarybutyloxycarbonyl-1,2-diaminoethane are diluted with 60 ml (5 eq) of a 1 M solution of HCl in diethylether while stirring at room temperature. After 48 h of stirring at room temperature, the fine-crystallinic precipitate is suctioned off over a G4 glass frit, freed of the HCl residues through multiple washing with anhydrous ether and dried under a vacuum. Obtained are 3.0 g (7.98 mmol) of the product as a fine-powdery yellow solid, corresponding to 66.9% of the theoretically possible yield. Elementary analysis for $C_{15}H_{19}N_3O_4Cl_2$ (375.9 g/mol); calculated: C: 47.89%, H: 5.05%, N: 11.17%, Cl: 18.86%; found: C: 46.97%, H: 5.42%, N: 10.03%, Cl: 17.63%.

N-(O-(3-maleinimidobenzoyl)-2-hydroxyethyl)-1,2-diaminoethane dichloroplatinum(II)

104 mg (0.25 mmol) of $K_2PtCl_4$ and 94.2 mg (0.25 mmol) of N-(O-(3-maleinimidobenzoyl)-2-hydroxyethyl)-1,2-diaminoethane dihydrochloride are dissolved in 5 ml each of 20% tetrahydrofuran/water and mixed portion-wise. The initially red $K_2PtCl_4$ solution is increasingly decolorized; a light-yellow precipitate is formed. Approximately 1 h after the last addition can the precipitate be suctioned off using a G4 glass frit. It is washed successively with small amounts of water, 20% tetrahydrofuran/water and finally with diethylether. After drying under a vacuum, obtained are 106 mg (0.18 mmol) of the product as a fine-crystalline substance, corresponding to 72% of the theoretically possible yield. Elementary analysis for $C_{15}H_{17}N_3O_4PtCl_2$ (569 g/mol); calculated: C: 31.63%, H: 2.99%, N: 7.38%, Pt: 34.29, Cl: 12.46%; found: C: 31.19%, H: 3.37%, N: 6.79 %, Pt: 32.35%, Cl: 12.95%

Step 3: Thiolation of the Carrier Protein

The method for the thiolation is illustrated in more detail through the following example: 32 mg of human serum transferrin (98% cyrstalline, Mr 80,000) [or 28.4 mg of human serum albumin (98% crystalline, Mr 66500), respectively] are dissolved in 1 ml of buffer (0 M sodium borate, 0.001 M EDTA, 0.15 M NaCl—pH=8.0) degassed with argon (c(transferrin/albumin)=$4.0 \times 10^{-4}$ M) and diluted with 100 µl of a freshly produced $4.0 \times 10^{-2}$ M iminothiolane solution (5.5 mg of iminothiolane dissolved in 1 ml of degassed buffer (0.1 M sodium borate, 0.15 M NaCl, 0.001 M EDTA—pH=8.0). After 60–70 minutes, the excess iminothiolane is separated through gel filtration (column 1.0 cm×10 cm, Sephadex G.25) with the running buffer of 0.05 M sodium borate, 0.15 M NaCl—pH 7.5 of thiolated transferrin or albumin. The protein concentration after completed gel filtration was was determined at 280 nm $\epsilon_{280}$=92300 $M^{-1}$ $cm^{-1}$, c[transferrin]=$2.4 \times 10^{-4}$ M) or $\epsilon_{280}$=35700 $M^{-1}$ $cm^{-1}$, (c[albumin]=$2.2 \times 10^{-4}$ M) and the number of the introduced HS groups was determined with Ellmanns reagent at 412 nm $\epsilon_{412}$=13600 $M^{-1}$ $cm^{-1}$) (c[HS group]=$7.4 \times 10^{-4}$ M or $7.7 \times 10^{-4}$ M). The ratio c[HS groups]/c[transferrin] was thus 3.1 and the ratio c[HS groups]/c[albumin] was 3.5. The following tables summarize the reaction conditions, by which different numbers of HS groups are introduced into transferrin or albumin:

TABLE 1a

Reaction conditions for the introduction of HS groups into transferrin

| c[iminothiolane]/ c[protein] | reaction time, min | temperature, ° C. | number of introduced HS groups/protein |
|---|---|---|---|
| 10:1 | 60–75 | 0–5 | 1 |
| 10:1 | 60–75 | 20–25 | 2–3 |
| 20:1 | 60–75 | 20–25 | 5–6 |
| 30:1 | 60–75 | 20–25 | 9–10 |
| 40:1 | 60–75 | 20–25 | 12–13 |
| 50:1 | 60–90 | 20–25 | 15–16 |
| 70:1 | 60–90 | 20–25 | 20–21 |

TABLE 1b

Reaction conditions for the introduction of HS groups in albumin

| c[iminothiolane]/ c[protein] | reaction time, min | temperature, ° C. | number of introduced HS groups/protein |
|---|---|---|---|
| 10:1 | 60–75 | 0–5 | 1 |
| 10:1 | 60–75 | 20–25 | 2–3 |

TABLE 1b-continued

Reaction conditions for the introduction of HS groups in albumin

| c[iminothiolane]/ c[protein] | reaction time, min | temperature, ° C. | number of introduced HS groups/protein |
|---|---|---|---|
| 20:1 | 60–75 | 20–25 | 5–6 |
| 30:1 | 60–75 | 20–25 | 9–10 |
| 50:1 | 60–95 | 20–25 | 15–16 |
| 70:1 | 60–90 | 20–25 | 30–32 |

The thus isolated protein sample was used directly for the following reaction in Step 4.

Step 4: Coupling of the Derivatives of the Cytostatic Compounds (Step 2) to the Thiolated Carrier Protein (Step 3) or to Polyethylene Glycols Methods FPLC for the production of conjugates: P-500 pump, LCC 501 controller (Pharmacia) and LKB 2151 uv-monitor, buffer: standard borate: 0.025 M sodium borate, 0.15 M NaCl—pH 7.5 or phosphate buffer: 0.004 M sodium phosphate, 0.15 M NaCl—ph 7.4. The protein concentration of the conjugate was determined with the BCA protein essay from Pierce (USA).

Transferrin conjugate with the 3'-amino amide derivative of doxorubicine and p-maleinimidophenylacetic acid (amide$_1$)

3.5 ml of thiolated transferrin sample (3.3 introduced HS groups) were diluted to 30 ml with standard borate and 1.0 ml of a solution of amide$_1$ (Mr 742.68) in DMF (1.8 mg dissolved in 1.0 ml of DMF) were added and mixed. After 10 min, the solution was concentrated to approximately 2.0 ml with CENTRIPREP®-10 concentrators from Amicon, FRG (60 min at 4° C. and 4500 U/min). The concentrated sample was centrifuged (5 min) with a Sigma 112 centrifuge and the excess applied on a Sephadex® G-25F column (column 1.0 cm×10 cm) and the conjugate was isolated (retention volume: 3.5–7.0 ml). The amount of bound doxorubicine was determined with the aid of epsilon values for doxorubicine $\epsilon_{495}$=10650 $M^{-1}$ $cm^{-1}$, from which the corresponding contribution of transferrin at this wavelength was subtracted $\epsilon[Tf]_{495}$=4100 $M^{-1}$ $cm^{-1}$. The concentration of the bound doxorubicin was 322 μM and that of transferrin was 101 μM.

Albumin conjugate of the carboxyl hydrazone derivative of [4-(4-bis(2-chloroethyl)amino-phenyl)]butyric acid hydrazide and 4-acetophenone carboxylic acid-(N-hydroxysuccinimide)-ester 66.5 mg of albumin, dissolved in 2.2 ml of 5ml phosphate buffer, were mixed with 0.1 ml of a solution of carboxyl-hydrazone derivative in DMF (1.2 mg dissolved in 0.1 ml of DMF), centrifuged after 10 min and the excess apllied on a Sephadex® G-25F column (column 1.0 cm×10 cm) and the conjugate was isolated (retention volume: 3.7–7.1 ml). The amount of bound chloroambucil was determined with the aid of the test according to Epstein (Epstein et al., Anal. Chem. 1955, 27, 1435–1439). It was 280 μM in this working method.

Polyethylene glycol conjugate consisting of CH$_3$O-PEG-SH 20,000 (α-methoxy-ω-thio-polyethylene glycol) and N-(O-(3-maleinimidobenzoyl)-2-hydroxyethyl)-1,2-diaminoethane dichloroplatinum(II)

100 mg of CH$_3$O-PEG-SH 20,000 (0.005 mmol) are dissolved in 5 ml of phosphate buffer and mixed with 5.7 mg (0.01 mmol) of N-(O-(3-maleinimidobenzoyl)-2-hydroxyethyl)-1,2-diaminoethane dichloroplatinum(II), dissolved in 250 μl of DMF. After 20 min, the reaction mixture was centrifuged and the excess applied on a Sephadex® G-25F column (column 2.0 cm×15 cm) and the conjugate was isolated. The amount of bound platinum complex was determined with the aid of the test according to Gonias and Pizzo (Gonias, S. L., Pizzo, S. V. *J.Biol.Chem.* 1982, 258, 5764–5769). It was 380 μM in this working method.

Polyethylene glycol conjugate consisting of HS-PEG-SH 20.000 (α.ω-bis-thio-polyethylene glycol) and N'-(2-maleinimidoethyloxycarbonyl)-5-fluorouracil 100 mg of HS-PEG-SH 20,000 (0.005 mmol) are dissolved in 5 ml of phosphate buffer and mixed with 3.0 mg (0.01 mmol) of N'-(2-maleinimidoethyloxycarbonyl)-5-fluorouracil, dissolved in 250 μl of DMF. After 30 min, the reaction mixture was centrifuged and the excess applied on a Sephadex® G-25F column (column 2.0 cm×15 cm) and the conjugate was isolated. The amount of bound 5-fluorouracil was determined at $\epsilon_{260}$=6520 $M^{-1}$ $cm^{-1}$. It was 460 μM in this working method.

Conjugate consisting of albumin and transferrin loaded with doxorubicin (amide$_1$)

30 mg of human serum albumin were dissolved in 2.0 ml of 0.1 M sodium borate degassed with argon, 0.001 M EDTA, 0.15 M NaCl—pH=8.0 at room temperature (RT). To this mixture, 183 μl of a solution of 2.9 mg of iminothiolane in 250 μl of degassed 0.1 M sodium borate, 0.001 M EDTA, 0.15 M NaCl—pH=8.0 were added, thoroughly mixed and incubated for 1 h at room temperature. Then, the excess iminothiolane was separated off through gel filtration. The measurement of protein concentration, as well as the concentration of free SH groups resulted in the following values: c[albumin]=1.44×10$^{-4}$ mol/l, c[SH groups]=1.25×10$^{-3}$ mol/l. The average number of SH groups per albumin molecule resulted from the quotient of both concentrations to be 8.7.

2.0 ml of this thiolated albumin solution were used for the further reaction. To neutralize 7 of the 8.7 SH groups per protein with 3'-aminoamide derivative of doxorubicin and p-maleinimidophenylacetic acid (amide$_1$), the protein solution was first diluted with standard borate buffer to 10 ml. Then, while shaking, 40 μl of a solution of 40 mg of amide$_1$ in 1 ml of DMF was added and incubated for 10 minutes at room temperature. After that, the sample was centrifuged (3,000 g, 4° C.) for 5 min. The excess was concentrated to a volume of approximately 1 ml (3,000 g, 3×15 min, 4° C.) using Centricon 3,000 concentrators® (company: Amicon). Then, 25 mg of human serum transferrin was dissolved in 1.2 ml of buffer (0.1 M sodium borate, 0.001 M EDTA, 0.15 M NaCl—pH=8.0) degassed with argon. To this mixture, 15 μl of a solution of 2.9 mg of iminothiolane in a 250 μl of buffer (0.1 M sodium borate, 0.001 M EDTA, 0.15 M NaCl—pH=8.0) degassed with argon were added, thoroughly mixed and incubated for 1 h at room temperature. Then, excess iminothiolane was separated off through gel filtration. The measurement of protein concentration as well as the concentration of free SH groups (test according to Ellmann) resulted in the following values: [transferrin]=1.20×10$^{-4}$ mol/l, [SH groups]=1.96×10$^{-4}$ mol/l. The average number of SH groups per transferrin molecule resulted from the quotient of both concentrations to be 1.6. 1.9 ml of the thus-thiolated transferrin solution were diluted to 10 ml for the further reaction, first, with standard borate buffer. Then, to the reaction mixture, 72 μl of a solution of 10 mg of 1,4-diamino-N,N'-di-m-maleinimidobenzyl-butane in 200 μl of DMF were added. After 10 min at room temperature, the turbid mixture was centrifuged (5 min, 3,000 g, 4° C.). The excess solution was poured off and concentrated in a Centricon 3,000 concentrator® to a volume of 600 μl. For removing of the excess bismaleinimide, it was filtered over a Sephadex 25. 1,500 μl of a solution with the thus-modified transferrin were added to 500 μl of the above albumin solution loaded with doxorubicin, mixed thoroughly and incubated for 15 min at room temperature. Thereafter, the solution was concentrated to a volume of 150 µl in Microcon 10 concentrators® (company: Amicon). The concentrated protein solution was separated through gel chromatography into its ingredients (monomers, dimers, oligomers). Dimensions of the column: h: 40 cm, ø: 1 cm, loop: 100 µl stationary phase: Superdex 200 Pharmacia, mobil phase: borate buffer, pH 6.8; gassed at +4° C. with $N_2$, flow: 1 ml/min, detection: photometric, $\lambda$=280 nm, retention volume: oligomers: 9.5 ml–11.5 ml, trimers: 11.7 ml–12.6 ml, dimers: 12.7 ml–14.4 ml, monomers: 14.5 ml–18.5 ml. The yield of the desired dimers with regard to the introduced $amide_1$ was 20–30%.

Biological Studies

As an example for the in vitro and in vivo effectiveness of the conjugates, given are biological data of the doxorubicin conjugates shown below, which are representative of the activity— or toxicity profile of the conjugates disclosed in the invention. The effectiveness of the conjugates was determined using a "colony-forming assay" and with the aid of the incorporation of BrdU(5-bromo-2-desoxyuridine) in the cell culture according to standard scientific practice. As examples, shown are the $IC_{70}$ values ("colony-forming assay"-seven xenografts) of the following doxorubicin conjugates: protein=transferrin (T) or albumin (A) compounds. Corresponding polyethylene glycol conjugates exhibited a similar behavior.

Furthermore, the above-shown conjugates exhibit, in comparison to the free doxorubicin, in the xeno-transplantable naked-mouse models, mammary carcinoma MDA-MB-435 and mammary carcinoma MCF-7, in total a clearly reduced toxicity (reduced lethalness and body weight reduction, fewer side-effects in the gastro-intestine area), as compared to the free doxorubicin, and a stabilization of the increase in the relative tumor volume with equal or improved tumor-inhibiting effectiveness, as is shown in the example of the transferrin conjugate T-DOXO-HYD in the table:

| Animals: Ncr:nu/nu female; tumor: mammary carcinoma MCF-7 s.c. Therapy: day(d) 16, day(d) 23 i.v. | | | | |
|---|---|---|---|---|
| number of mice | substance | dose (mg/kg/ inj.) | mortality (d) | body weight loss (%) d 13–23 | optimum T/C (%) |
| 8 | NaCl | | | 4 | |
| 8 | doxorubicin | 4 | | –5 | 61 |
| 8 | doxorubicin | 8 | 1 (26) | –15 | 39 |
| 7 | doxorubicin | 12 | 7 (25–33) | –21 | |

IC70 values in seven human tumor xenografts (colony-forming assay)

| human tumor xenograft | T-DOXO-HYD | T-DOXO-ARZID | DOXO-RUBICIN | A-DOXO-ARZID | A-DOXO-RYD |
|---|---|---|---|---|---|
| bladder BXF 1299 | 1.48 | 0.09 | 0.50 | 0.06 | 0.10 |
| lung LXFL 529 | 0.054 | 0.06 | 0.02 | 0.03 | 0.04 |
| lung LXFS 538 | 0.04 | 0.04 | 0.02 | 0.001 | 0.01 |
| mamma MAXFMX1 | 0.04 | 0.04 | 0.02 | 0.01 | 0.10 |
| melanoma MEXF989 | 0.29 | 0.23 | 0.30 | 0.34 | 0.30 |
| prostate PC3MX | 0.02 | 0.03 | 0.03 | 0.02 | 0.06 |
| prostate DU145X | 0.12 | 0.08 | 0.35 | 0.24 | 0.21 |

Under these experimental conditions, the synthesized conjugates as listed above showed an effectiveness that was equal to or higher than that of the unbound cytostatic -continued Animals: Ncr:nu/nu female; tumor: mammary carcinoma MCF-7 s.c.
Therapy: day(d) 16, day(d) 23 i.v.

| number of mice | substance | dose (mg/kg/ inj.) | mortality (d) | body weight loss (%) d 13–23 | optimum T/C (%) |
|---|---|---|---|---|---|
| 8 | T-DOXO-HYD | 4 | | −4 | 82 |
| 8 | T-DOXO-HYD | 8 | | −4 | 42 |
| 8 | T-DOXO-HYD | 12 | | −6 | 21 |

The dose refers to the amount of doxorubicin available. In the case of an equimolar dose (8mg/kg), T-DOXO-HYD exhibits an effectiveness that is comparable to that of doxorubicin at reduced lethalness and body weight reduction. In the case of the highest dose employed in the experiment (12 mg/kg), there appears a very high lethalness (5 of 7 and 7 of 7 animals, respectively) in the therapy with doxorubicin. The therapy with the transferrin conjugate at this dose exhibits no lethalness, the anti-tumor effectiveness being better.

What is claimed is:

1. A conjugate of a cytostatic compound and albumin, wherein 2 to 30 equivalents of said cytostatic compound are each coupled via a spacer comprising a group which is derived from a maleinimido group, to thiolated albumin, wherein the thiolated albumin is conjugated via a group which is derived from a bismaleinimido compound to transferrin or a monoclonal antibody which is directed to a tumor associated antigen;

and wherein said thiolated albumin has 1 to 30 HS groups on the average, and wherein said group which is derived from a bismaleinimido compound is formed through conjugating said thiolated albumin, which is coupled to 2 to 30 equivalents of said cytostatic compounds, with a bismaleinimide compound of the formula XI:

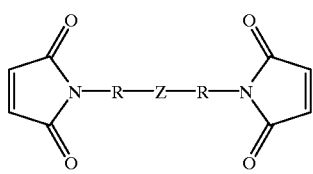

Formula XI wherein Z=—CO—NH—$(CH_2)_n$—NH—CO—, —CO—O—$(CH_2)_n$—O—CO—, —CH=N—$(CH_2)_n$—N=CH—, —CH=N—NH—$(CH_2)_n$—NH—N=CH— or —CH=N—NH—CO—$(CH_2)_n$—CO—NH—N=CH— and n=2–12, and wherein R is an aliphatic carbon chain having 1–6 carbon atoms or a substituted or unsubstituted benzyl group or a substituted or unsubstituted phenylene group.

2. The conjugate according to claim 1, wherein said cytostatic compound is selected from the group consisting of anthracyclines, nitrogen mustard gas derivatives, purine or pyrimidine antagonists, folic acid antagonists, taxoids, camptothecines, podophyllotoxin derivatives, vinca alkaloids and cis-configured platinum(II)-complexes.

3. The conjugate according to claim 1, wherein said cytostatic compound is selected from the group consisting of doxorubicine, daunorubicine, epirubicine, idarubicine, mitoxandrone, chloroambucil, melphalan, 5-fluorouracil, 5'-deoxy-5-fluorouridine, thioguanine, methotrexate, paclitaxel, docetaxel, topotecane, 9-aminocamptothecine, etoposide, teniposide, mitopodozide, vinblastine, vincristine, vindesine, vinorelbine and compounds of the general formulas I, II, III or IV:

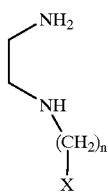

Formula I

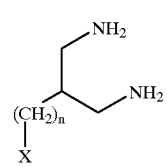

Formula II

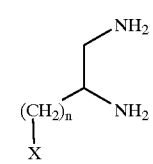

Formula III

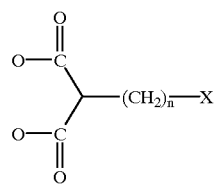

Formula IV wherein n=0–6, X=—$NH_2$, —OH, —COOH, —O—CO—R—COR* or —NH—CO—R—COR*, wherein R is an aliphatic carbon chain having 1–6 carbon atoms or is a substituted or unsubstituted phenylene group and R* is H, phenyl or alkyl having 1–6 carbon atoms.

4. The conjugate according to claim 1, wherein said cytostatic compound having said spacer comprising a group which is derived from a maleinimido group, is formed through reaction of said cytostatic compound with a maleinimide compound of the formula V, VI or VII:

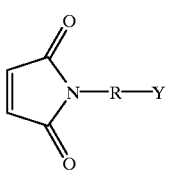

Formula V

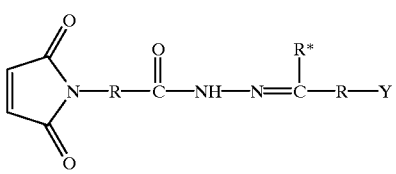

Formula VI

-continued

Formula VII

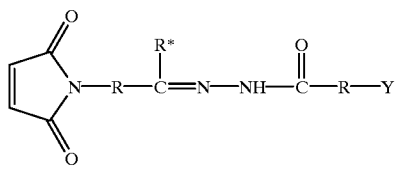

wherein R is an aliphatic carbon chain having 1–6 carbon atoms or a substituted or unsubstituted benzyl group or a substituted or unsubstituted phenylene group, Y=—OH, —COOH, —COCl, —CONH—$(CH_2)_n$—OH, —COO—$(CH_2)_n$—$NH_2$, —COO—$(CH_2)_n$—$NHNH_2$, —$SO_3H$, —$SO_3Cl$, —$SO_2$—$NHNH_2$, —O—COCl, —CHO or —COR*, wherein n=1–6 and R* represents H, phenyl or alkyl having 1–6 carbon atoms, and the thus obtained maleinimide derivative of said cytostatic compound is coupled to said thiolated albumin or said thiolated transferrin or said polyethylene glycol, wherein the chemical linkage between said cytostatic compound and said maleinimide compound occurs through an amide, ester, imine, hydrazone, carboxyl hydrazone, oxycarbonyl, acetal or ketal bond.

5. A method for the production of a conjugate of a cytostatic compound and albumin according to claim 1, comprising the steps of:
   (a) reacting a cytostatic compound with a maleinimide compound, such that maleinimide derivatives of said cytostatic compound are produced, wherein the chemical linkage between said cytostatic compound and said maleinimide compound occurs through an amide, ester, imine, hydrazone, carboxyl hydrazone, oxycarbonyl, acetal or ketal bond; and
   (b) loading thiolated albumin with 2 to 30 equivalents of said maleinimide derivatives obtained in step (a) of the cytostatic compound and conjugating with transferrin or a monoclonal antibody directed to a tumor-associated antigen via a group which is derived from a bismaleinimido compound.

6. A pharmaceutical composition, containing the conjugate according to claim 1, optionally together with carriers and auxiliary agents.

7. Method for the treatment of a cancer disease, comprising the step of treating an organism having a cancer disease with the conjugate of claim 1.

8. Method for the treatment of a cancer disease, wherein said cancer disease comprises bladder, lung, mamma, melanoma or prostrate carcinomas, comprising the step of treating an organism having said cancer disease with a conjugate of a cytostatic compound and transferrin or albumin or a polyethylene glycol, wherein:
   (a) said cytostatic compound is coupled via a spacer comprising a group which is derived from a maleinimido group, to thiolated transferrin or thiolated albumin or to polyethylene glycol having at least one HS or $H_2N$ group; or
   (b) 2 to 30 equivalents of said cytostatic compound are each coupled via a spacer comprising a group which is derived from a maleinimido group, to thiolated albumin, wherein the thiolated albumin is conjugated via a group which is derived from a bismaleinimido compound to transferrin or a monoclonal antibody which is directed to a tumor associated antigen;
   wherein said thiolated transferrin or said thiolated albumin has 1 to 30 HS groups on the average, and said polyethylene glycol has a mass of about between 5,000 and 200,000 Da, and
   wherein said group which is derived from a bismaleinimido compound is formed through conjugating said thiolated albumin, which is coupled to 2 to 30 equivalents of said cytostatic compounds, with a bismaleinimide compound of tie formula XI:

Formula XI

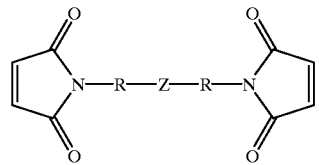

wherein Z=—CO—NH—$(CH_2)_n$—NH—CO—, —CO—O—$(CH_2)_n$—O—CO—, —CH=N—$(CH_2)_n$—N=CH—, —CH=N—NH—$(CH_2)_n$—NH—N=CH— or —CH=N—NH—CO—$(CH_2)_n$—CO—NH—N=CH— and n=2–12, and wherein R is an aliphatic carbon chain having 1–6 carbon atoms or a substituted or unsubstituted benzyl group or a substituted or unsubstituted phenylene group.

9. Method according to claim 7, wherein said cancer disease comprises bladder, lung, mamma, melanoma or prostrate carcinomas.

* * * * *